US011155856B2

(12) United States Patent
Jewell et al.

(10) Patent No.: US 11,155,856 B2
(45) Date of Patent: Oct. 26, 2021

(54) METHODS FOR IDENTIFYING A COMPANION ANIMAL SUSCEPTIBLE TO TREATMENT THAT REDUCES THE RISK OF STONE FORMATION AND COMPOSITIONS FOR REDUCING SUCH RISK

(71) Applicant: Hill's Pet Nutrition, Inc., Topeka, KS (US)

(72) Inventors: Dennis Jewell, Lawrence, KS (US); Jeffrey Brockman, Lawrence, KS (US); Kiran Panickar, Lawrence, KS (US); Laura Morgan, Saint George, KS (US)

(73) Assignee: Hills Pet Nutrition, Inc., Topeka, KS (US)

( * ) Notice: Subject to any disclaimer, the term of this patent is extended or adjusted under 35 U.S.C. 154(b) by 0 days.

(21) Appl. No.: 16/718,836

(22) Filed: Dec. 18, 2019

(65) Prior Publication Data

US 2020/0239941 A1    Jul. 30, 2020

Related U.S. Application Data

(60) Provisional application No. 62/796,758, filed on Jan. 25, 2019.

(51) Int. Cl.
*C12Q 1/6827* (2018.01)
*A23K 50/40* (2016.01)
(Continued)

(52) U.S. Cl.
CPC ............ *C12Q 1/6827* (2013.01); *A23K 10/30* (2016.05); *A23K 50/40* (2016.05); *A61K 36/52* (2013.01);
(Continued)

(58) Field of Classification Search
CPC ...... A23K 50/40; A23K 20/158; A23K 50/42; A23K 20/163; A23K 20/26; A23K 20/147; A23K 20/22; A23K 20/24; A23K 50/48; A23K 10/30; A23K 20/174; A23K 10/20; A23K 20/105; A23K 20/10; A23K 40/00; A23K 10/37; A23K 20/189; A23K 20/30; A23K 40/20; A23K 20/179; A23K 20/20; A23K 30/00; A23K 40/25; A23K 40/30; A23K 10/14; A23K 10/18; A23K 20/142; A23K 10/33; A23K 1/1846; A23K 50/10; A23K 50/75; A23V 2002/00; A23V 2250/1578; A23V 2250/1614; A23V 2250/1618; A23V 2250/5026; A23V 2250/5486; A23V 2250/0604; A23V 2250/7042; A23V 2250/0606; A23V 2250/061; A23V 2250/0624; A23V 2250/0626; A23V 2250/063; A23V 2250/0638; A23V 2250/0644; A23V 2250/0648; A23V 2250/0652; A23V 2250/0654; A23V 2250/1584; A23V 2250/1588; A23V 2250/1592; A23V 2250/1598; A23V 2250/16; A23V 2250/1612; A23V 2250/1626; A23V 2250/1642; A23V 2250/304; A23V 2250/31; A23V 2250/702; A23V 2250/7044; A23V 2250/7046; A23V 2250/705; A23V 2250/7052; A23V 2250/7058; A23V 2250/706; A23V 2250/708; A23V 2250/71; A23V 2250/712; A23V 2250/76; A23V 2200/00; A23V 2250/0622; G01N 33/84; G01N 2800/345; G01N 2800/348; G01N 33/5091; G01N 33/52; G01N 33/493; G01N 2800/52; G01N 33/6806; A61P 13/00; A61P 13/04; A61P 19/02; A61P 1/00; A61P 13/12; A61P 29/00; A61P 31/00; A61P 39/06; G06Q 99/00; Y10T 436/17; A61K 2300/00; A61K 31/01; A61K 31/202; A61K 31/726; A61K 31/405; A61K 36/9068; A61K 45/06;
(Continued)

(56) References Cited

U.S. PATENT DOCUMENTS 5,339,771 A    8/1994  Axelrod
5,419,283 A    5/1995  Leo

FOREIGN PATENT DOCUMENTS

WO    2015/072972 A1    5/2015
WO    2018/125539 A1    7/2018

OTHER PUBLICATIONS

Akiyama et al., 2012, "A Metabolomic Approach to Clarifying the Effect of AST-120 on 5/6 Nephrectomized Rats by Capillary Electrophoresis with Mass Spectrometry (CE-MS)," Toxins 4(11):1309-1322.

(Continued)

*Primary Examiner* — Aaron J Kosar

(57) ABSTRACT

Methods of analyzing a biological sample obtained from the feline subject for the presence of two copies of major allele G of SNP A1_212891692 and/or to the concentration of betaine and/or 2-oxoarginine in the sample are disclosed. The methods are used in methods to identify a feline subject that would benefit from a treatment that reduces risk of calcium oxalate stone formation and in methods of treating a feline subject to reduce risk of calcium oxalate stone formation The treatment on comprises administering to the feline subject a composition that comprises an effective amount of one or more of ingredients selected from the group consisting of betaine, green tea, fenugreek and tulsi. Feline food composition that comprise effective amounts of betaine, green tea, fenugreek and tulsi are disclosed.

40 Claims, 2 Drawing Sheets

Specification includes a Sequence Listing.

(51) Int. Cl.
| | |
|---|---|
| A23K 10/30 | (2016.01) |
| A61K 36/52 | (2006.01) |
| A61K 36/82 | (2006.01) |
| A61K 36/88 | (2006.01) |
| C12Q 1/6883 | (2018.01) |

(52) U.S. Cl.
CPC .............. *A61K 36/82* (2013.01); *A61K 36/88* (2013.01); *C12Q 1/6883* (2013.01); *C12Q 2600/106* (2013.01); *C12Q 2600/124* (2013.01); *C12Q 2600/156* (2013.01)

(58) Field of Classification Search
CPC .... A61K 9/0056; A61K 31/015; A61K 31/19; A61K 36/52; A61K 36/82; A61K 36/88; A61K 31/20; A61K 31/355; A61K 31/375; A61K 31/715; A61K 31/716; A61K 31/717; A61K 31/719; A61K 31/721; A61K 31/723; A61K 31/734; A61K 31/736; A61K 47/36; A23L 13/43; A23L 13/422; A23L 29/256; A23L 33/15; A23L 33/16; A23L 13/60; A23L 17/65; A23L 17/70; A23L 33/10; A23L 33/12; A23L 33/14; A23L 33/175; A23L 13/03; A23L 13/20; A23L 13/428; A23L 13/432; A23L 27/201; A23L 27/215; A23L 27/26; A23L 27/84; A23L 33/115; A23L 33/155; A23L 33/17; A23L 33/40; A23L 5/21; A23J 3/227; C12Q 1/6827; C12Q 2600/124; C12Q 2600/156; C12Q 1/6883; C12Q 2600/106; Y02P 60/87; Y02P 60/877; A23B 4/22; A23Y 2220/03; A23Y 2220/29; A23Y 2240/75; A23Y 2300/49; C12N 1/16; C12N 1/20; C12N 9/1044; C12Y 203/02013; Y02E 50/17; Y02E 50/10; A23D 7/0053; A23D 7/04; A23D 9/00; A23D 9/007; A23D 9/013; A23G 2200/08; A23P 20/12; H04L 25/03834; H04L 27/2017

See application file for complete search history.

(56) References Cited

OTHER PUBLICATIONS

Ballet et al., 2018, "New enzymatic and mass spectrometric methodology for the selective investigation of gut microbiota-derived metabolites," Chemical Science 9:6233-6239.

Burrage et al., 2019, "Untargeted metabolomic profiling reveals multiple pathway perturbations and new clinical biomarkers in urea cycle disorders," Genetics in Medicine 21:1977-1986.

Evans et al., 2009, "Integrated, nontargeted ultrahigh performance liquid chromatography/electrospray ionization tandem mass spectrometry platform for the identification and relative quantification of the small-molecule complement of biological systems," Analytical Chemistry 81:6656-6667.

Fernàndez-Roig, 2013, "Low folate status enhances pregnancy changes in plasma betaine and dimethylglycine concentrations and the association between betaine and homocysteine," American J. Clinical Nutrition 97:1252-1259.

Hall et al., 2014, "Comparison of Serum Concentrations of Symmetric Dimethylarginine and Creatinine as Kidney Function Biomarkers in Cats with Chronic Kidney Disease," J. Veterinary Internal Medicine 28:1676-1683.

Hall et al., 2014, "Comparison of serum concentrations of symmetric dimethylarginine and creatinine as kidney function biomarkers in healthy geriatric cats fed reduced protein foods enriched with fish oil, L-carnitine, and medium-chain triglycerides," The Veterinary Journal 202:588-596.

Hall et al., 2017, "Increased dietary long-chain polyunsaturated fatty acids alter serum fatty acid concentrations and lower risk of urine stone formation in cats," PLoS ONE 12(10):e88544.

Hall et al., 2017, "Serum concentrations of symmetric dimethylarginine and creatinine in cats with kidney stones," PLoS ONE 12(4):e0174854.

Holm et al., 2005, "Betaine and folate status as cooperative determinants of plasma homocysteine in humans," Arteriosclerosis Thrombosis Vascular Biology 25:379-385.

Kennedy et al., 2016, "Metabolomic profiling of human urine as a screen for multiple inborn errors of metabolism," Genetic Testing and Molecular Biomarkers 20:485-495.

Kikuchi et al., 2010, "Metabolomic search for uremic toxins as indicators of the effect of an oral sorbent AST-120 by liquid chromatography/tandem mass spectrometry," J. Chromatography B Analytical Technology Biomed Life Science 878:2997-3002.

Kittle et al., 2014, "Alanine-glyoxylate aminotransferase 2 (AGXT2) Polymorphisms Have Considerable Impact on Methylarginine and b-amino isobutyrate Metabolism in Healthy Volunteers," PLoS ONE 9(2):e88544.

Midttun et al., 2013, "High-throughput, low-volume, multianalyte quantification of plasma metabolites related to one-carbon metabolism using HPLC-MS/MS," Analytical Bioanalytical Chemistry 405:2009-2017.

Miller et al., 2015, "Untargeted metabolomic analysis for the clinical screening of inborn errors of metabolism," J. Inherit Metabolic Disease 38:1029-1039.

Zhou et al., 2014, "Association of the AGXT2 V140I Polymorphism with risk for coronary Heart Disease in a Chinese Population," J. Atherosclerosis Thrombosis 21(10):1022-1030.

Frassetto et al., 2011, "Treatment and Prevention of Kidney Stones: An Update", American Family Physician, 1234-1242.

Gao et al., 2016, "Metabolomics analysis hydroxy-L-proline-induced calcium oxalate nephrolithiasis in rats based on ultra-high performance liquid chromatography quadrupole time-of-flight mass spectrometry", Scientific Reports, 6(1), (12 pages).

Hu et al., 2017, "AGXT2: An unnegligible aminotransferase in cardiovascular and urinary systems", Journal of Molecular and Cellular Cardiology, 113:33-38.

International Search Report and the Written Opinion of the International Searching Authority issued in International Application PCT/US2019/067091 dated Jun. 25, 2020.

Jackson et al., 2014, "Design of diets based on gene expression data produces foods which improve renal health and ameliorate sarcopenic obesity", FASEB Journal, 28(1):246.3, (2 pages).

Oppici et al., 2015, "Liver peroxisomal alanine:glyoxylate aminotransferase and the effects of mutations associated with Primary Hyperoxaluria Type I: An overview", Biochimica et Biophysica Acta (BBA)—Proteins & Proteomics, 1854(9):1212-1219.

METHODS FOR IDENTIFYING A COMPANION ANIMAL SUSCEPTIBLE TO TREATMENT THAT REDUCES THE RISK OF STONE FORMATION AND COMPOSITIONS FOR REDUCING SUCH RISK

BACKGROUND

Bladder stones are relatively common in cats. Cats that have disease that affects the lower urinary tract, such as struvite or calcium oxalate bladder stones typically have one or more symptoms such as urinating outside the litter box, straining to urinate, frequent urination producing only a small amount of urine at any one time, blood in the urine and genital licking. Results from X-rays, and ultrasound of the abdomen may lead to the discovery of bladder stones. Urinalysis results such as urine pH, the presence of crystals and the absence of infection may lead to the diagnosis of calcium oxalate bladder stones. Bladder stones can be removed by surgery, cystoscopy (in female cats) or lithotripsy. A sample of the stones can be analyzed to confirm the diagnosis.

Historically, bladder stones in cats were made of struvite, which is magnesium ammonium phosphate. To prevent struvite bladder stones, many feline diets are formulated to make cats produce more acidic urine, which dissolves struvite and/or prevents struvite stone formation. Such diets result in urinary acidification which is very effective to prevent struvite stone formation. An undesirable consequence of such diets, however, is that they also create high blood calcium levels that put cats at increased risk for calcium oxalate stones. That is, many of the feline diets formulated to prevent struvite stone formation also increase conditions that promote calcium oxalate stones.

Calcium oxalate stones are a significant cause of death and discomfort in cats. While the incidence of calcium oxalate bladder stones can be reduced by feeding that cat a non-acidifying diet, such a diet increases the risk of struvite bladder stones. Diets with a high-water content and/or supplemented with potassium citrate, may result in a urine with a pH over 6.5, a specific gravity of about 1.020, and an absence of crystals, may reduce risk of calcium oxalate stone formation. Such diets, however, are often insufficient to significantly reduce risk of calcium oxalate stones.

Strategies to reduce calcium oxalate stone formation include those that address any underlying condition that leads to high blood calcium levels. Calcium oxalate stones form from calcium oxalate crystals. Oxalate is the product of oxidation of glyoxylate.

In addition to be being a substrate to form oxalate, glyoxylate may alternatively be catalyzed to glycine by alanine-glyoxylate aminotransferase 2 (AGTX2) using L-alanine as the amino donor. AGTX2, which is encoded by the AGXT2 gene, is a class III pyridoxal-phosphate-dependent mitochondrial aminotransferase, which is considered a promiscuous aminotransferase. AGTX2 is an important regulator of methylarginines and is involved in the control of blood pressure in the kidney. By metabolizing glyoxylate into products other than oxalate, enzymes such as AGXT, AGXT2 and others reduce the level of glyoxylate that would otherwise be available as a substrate for oxalate production, and accordingly activity by such enzymes reduce oxalate levels.

Polymorphisms in the AGXT2 gene affect methylarginine and beta-amino isobutyrate metabolism influencing concentration of dimethylarginines and beta-amino isobutyrate. In addition, AGXT2 polymorphisms are associated with carotid atherosclerosis.

Symmetric dimethyl arginine (SDMA) is a substrate of AGXT2. SDMA has been shown to be associated with (increased) with changes in renal function in the cat (prior to a decline in renal function) (Hall et al, 2014, Comparison of Serum Concentrations of Symmetric Dimethylarginine and Creatinine as Kidney Function Biomarkers in Cats with Chronic Kidney Disease J Vet Intern Med; 28:1676-1683; Hall et al., 2014, Comparison of serum concentrations of symmetric dimethylarginine and creatinine as kidney function biomarkers in healthy geriatric cats fed reduced protein foods enriched with fish oil, L-carnitine, and medium-chain triglycerides The Veterinary Journal 202 588-596) as well as showing a relationship between SDMA and stone formation in the cat (Hall et al, 2017 Serum concentrations of symmetric dimethylarginine and creatinine in cats with kidney stones PLoS ONE 12 (4): e0174854).

Some researchers, noting that SDMA and ADMA are substrates of AGXT2, have shown an association with AGXT2 polymorphisms and their concentration. For example, Kittle et al (2014, Alanine-glyoxylate aminotransferase 2 (AGXT2) Polymorphisms Have Considerable Impact on Methylarginine and b-amino isobutyrate Metabolism in Healthy Volunteers, PLoS ONE 9(2): e88544) showed that specific polymorphisms influenced concentration of dimethylarginines and beta-amino isobutyrate and were associated with b-amino isobutyrate concentrations as well as SDMA concentrations.

A significant positive interaction with the dimethylarginines and beta-aminoisobutyrate has been noted. The association with methyl arginines and AGXT2 polymorphisms was also shown by Zhou et al (2014) Association of the AGXT2 V140I Polymorphism with risk for coronary Heart Disease in a Chinese Population, J Atheroscler Thromb. 21(10):1022-30. In particular increased ADMA was shown to be influenced by AGXT2 genotypes in a population of smokers and those with diabetes mellitus.

A urine calcium oxalate titrimetric test (COTT) is a method that is useful to assess risk of calcium oxalate stone formation (Hall et al, 2017 Increased dietary long-chain polyunsaturated fatty acids alter serum fatty acid concentrations and lower risk of urine stone formation in cats. PLoS ONE 12(10):e88544). The concentration of ionized calcium and the amount of oxalate that is added to initiate crystallization per liter in a urine sample is calculated as a ratio $[Ca^{+2}]/(added\ Ox^{-2})$. An increasing index value denotes samples at greater risk of calcium oxalate crystallization, whereas decreasing index values denotes those with less risk. Calcium oxalate titration test (COTT) results can be improved by dietary intervention to lower the stone formation risk for calcium oxalate stones in cats.

Single nucleotide polymorphisms (SNPs) are a common type of genetic variation. SNPs are single base pair mutations at a specific locus. That is, a SNP is a difference in a single nucleotide in a DNA sequence that occurs at a specific position in a genome. Typically, for a SNP at a specific position, there are two possible nucleotide variations, which are referred to as alleles for that position. Within a population, the nucleotide variation that most commonly appears at a specific base position in a genome is referred to as the major allele; the nucleotide variation that is less common at that specific base position is referred to as the minor allele. Felines, like most multicellular organisms have two sets of chromosomes. Thus, each cat has two copies of each gene or locus and therefore two copies of each SNP. Accordingly, for each SNP in the cat's genome, the cat may have two copies of the major allele, or one copy of the minor allele and one copy of the minor allele, or two copies of the minor allele.

SNPs can act as biological markers. Some SNPs have been found helpful in predicting drug responses and risk of developing particular diseases. SNP genotyping refers to detection of SNPs within the genome. There are numerous methods for detecting SNPs and performing SNP genotyping.

There is a need for improved compositions and methods that reduce the risk of developing calcium oxalate bladder stones, including compositions and methods that reduce the risk of developing calcium oxalate bladder stones in at least a subpopulation of cats having genetic markers or phenotypic traits. There is a need for improved compositions and methods that prevent calcium oxalate stone formation in at least a subpopulation of cats having genetic markers or phenotypic traits. There is a need to develop methods to identify cats that will benefit from treatment to reduce the likelihood or risk of developing calcium oxalate stones. There is a need for kits, reagents, other articles, and compositions useful in such methods.

BRIEF SUMMARY

Methods that comprise analyzing a biological sample obtained from the feline subject for the presence of two copies of major allele G of SNP A1_212891692 are provided. A feline subject having two copies of major allele G of SNP A1_212891692 indicates that the feline subject that would benefit from a treatment that reduces risk of calcium oxalate stone formation. The treatment that reduces risk of calcium oxalate stone formation comprises administering to the feline subject a composition that comprises an effective amount of one or more of ingredients selected from the group consisting of betaine, green tea, fenugreek and tulsi. In some embodiments, the sample is analyzed by performing DNA sequencing, restriction enzyme digest, polymerase chain reaction (PCR), hybridization, real-time PCR, reverse transcriptase PCR, or ligase chain reaction. In some embodiments, the sample is a genomic DNA sample. In some embodiments, the sample is obtained from blood, saliva, follicle root, nasal swab or oral swab of the feline subject, preferably saliva. In some embodiments, the sample is analyzed by performing at least one nucleic acid analysis technique selected from: analysis using a whole genome SNP chip, single-stranded conformational polymorphism (SSCP) assay, restriction fragment length polymorphism (RFLP), automated fluorescent sequencing; clamped denaturing gel electrophoresis (CDGE); denaturing gradient gel electrophoresis (DGGE), mobility shift analysis, restriction enzyme analysis, heteroduplex analysis, chemical mismatch cleavage (CMC), RNase protection assays, use of polypeptides that recognize nucleotide mismatches, allele-specific PCR, sequence analysis, and SNP genotyping. In some embodiments, the sample is analyzed by performing at least one nucleic acid analysis technique selected from: hybridization-based methods, enzyme-based methods, post-amplification methods based on physical properties of DNA, and sequencing methods.

Methods that comprise analyzing a biological sample obtained from the feline subject to determine the feline subject's betaine concentration are provided. The feline subject's betaine concentration may be compared to a positive reference betaine concentration value or a measured value from a positive control. The positive reference betaine concentration value that is representative of betaine concentration of a cat that would benefit from a treatment that reduces risk of calcium oxalate stone formation. The positive control sample contains betaine at a concentration representative of the betaine concentration of a cat that would benefit from a treatment that reduces risk of calcium oxalate stone formation. The treatment comprises administering to the feline subject a composition that comprises an effective amount of one or more of ingredients selected from the group consisting of betaine, green tea, fenugreek and tulsi. A feline subject with betaine concentration being equal to or less than the positive reference betaine concentration value or the measured betaine concentration of the positive control indicates that the feline subject would benefit from a treatment.

Methods that comprise analyzing a biological sample obtained from the feline subject to determine the feline subject's 2-oxoarginine concentration are provided. The feline subject's 2-oxoarginine concentration may be compared to a positive reference 2-oxoarginine concentration value or a measured value from a positive control. The positive reference 2-oxoarginine concentration value that is representative of 2-oxoarginine concentration of a cat that would benefit from a treatment that reduces risk of calcium oxalate stone formation. The positive control sample contains 2-oxoarginine at a concentration representative of the 2-oxoarginine concentration of a cat that would benefit from a treatment that reduces risk of calcium oxalate stone formation. The treatment comprises administering to the feline subject a composition that comprises an effective amount of one or more of ingredients selected from the group consisting of betaine, green tea, fenugreek and tulsi. A feline subject with 2-oxoarginine concentration being equal to or greater than the positive reference 2-oxoarginine concentration value or the measured 2-oxoarginine concentration of the positive control indicates that the feline subject would benefit from a treatment.

Methods of reducing risk of calcium oxalate stone formation in a feline subject are provided. The methods comprise the steps of identifying the feline subject as being a feline subject that would benefit from a treatment that reduces risk of calcium oxalate stone formation; and administering to the feline subject a composition that comprises effective amounts of one or more of betaine, green tea, fenugreek and tulsi. The feline subject is identified as being a feline subject that would benefit from a treatment that reduces risk of calcium oxalate stone formation by detecting the presence of two copies of major allele G of SNP A1_212891692 and/or detecting the feline subject's betaine level and determining it indicates that feline subject would benefit from a treatment that reduces risk of calcium oxalate stone formation and/or detecting the feline subject's 2-oxoarginine level and determining it indicates that feline subject would benefit from a treatment that reduces risk of calcium oxalate stone formation. In some embodiments, the feline subject is fed a nutritional composition that comprises effective amounts of one or more of betaine, green tea, fenugreek and tulsi. In some embodiments, the feline subject is fed a nutritional composition that comprises effective amounts of betaine, green tea, fenugreek and tulsi. In some embodiments, the feline subject is fed a nutritional composition that comprises a percentage of nutritional intake based on the dry matter daily intake, 0.25-1.0% betaine and/or 0.20-0.30% green tea and/or 0.01% to 0.05% fenugreek and/or 0.0005-0.003% tulsi. In some embodiments, the feline subject is fed a nutritional composition that comprises a percentage of nutritional intake based on the dry matter daily intake, 0.25-1.0% betaine, 0.20-0.30% green tea, 0.01% to 0.05% fenugreek and 0.0005-0.003% tulsi.

Feline food composition are provided that comprise an amount of betaine that is equal to 0.25-1.0% of nutritional intake per day based on the dry matter daily intake, and/or an amount of green tea that is equal to 0.20-0.30% of nutritional intake per day based on the dry matter daily intake and/or an amount of fenugreek that is equal to 0.01% to 0.05% of nutritional intake per day based on the dry matter daily intake and/or an amount of tulsi that is equal to/or 0.0005-0.003% of nutritional intake per day based on the dry matter daily intake.

DETAILED DESCRIPTION

Figure 1:
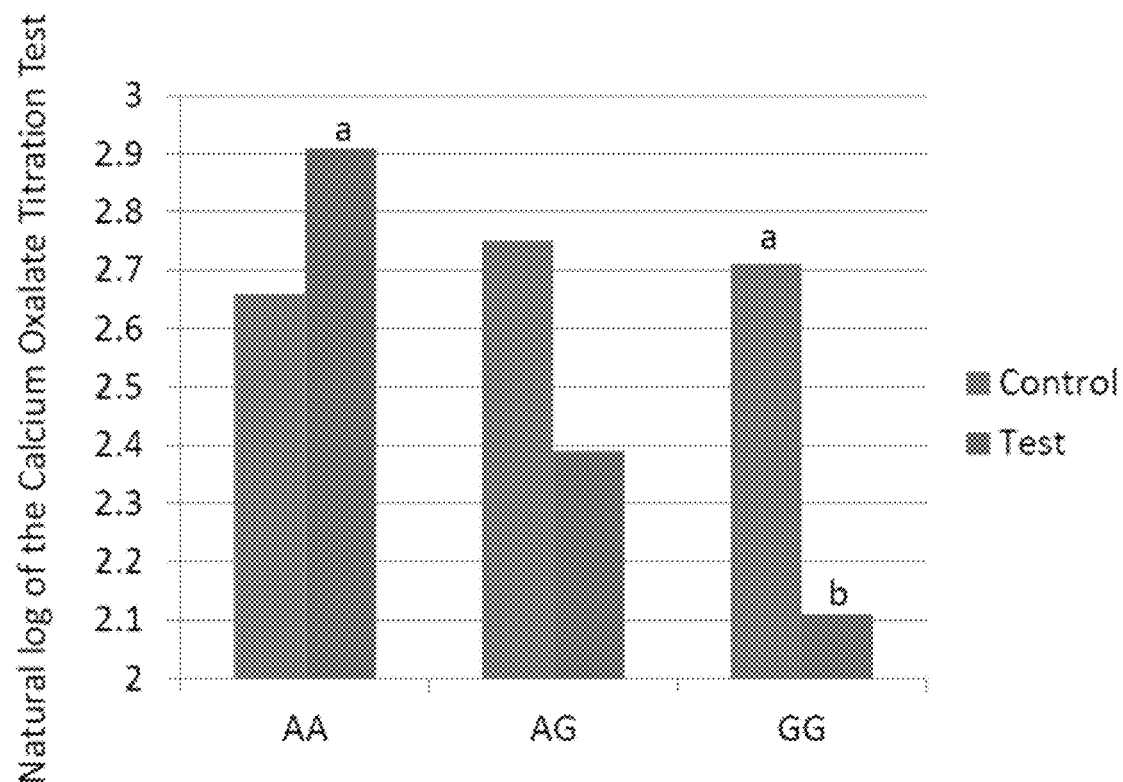
FIG. 1 shows results from a Multivariant Anova procedure which show that the GG genotype has higher concentration of circulating cytokines than that of the AA genotype.

The following description of the preferred embodiment(s) is merely exemplary in nature and is in no way intended to limit the invention, its application, or uses.

As used herein and in the appended claims, the singular forms "a", "an", and "the" include plural reference unless the context clearly dictates otherwise.

The term "cat" includes those cats which are companion animals known as domestic cats or house cats, or *Felis domesticus*. The term cat is synonymous with the term feline.

Methods are provided for identifying a feline subject that will benefit from a treatment to reduce the likelihood of developing calcium oxalate bladder stones. The treatment to reduce risk of calcium oxalate stone formation that comprises administering effective amounts of one or more of the components selected from the group consisting of betaine, green tea, fenugreek and tulsi. In some embodiments, the methods for identifying a feline subject that will benefit from such treatment to reduce the likelihood of developing calcium oxalate bladder stones comprise analyzing a sample from the feline subject to determine if the feline subject has a GG genotype for SNP A1_212891692 (felCat8). In some embodiments, the methods for identifying a feline subject that will benefit from such treatment to reduce the likelihood of developing calcium oxalate bladder stones comprise analyzing a sample from the feline subject to determine if the level of circulating betaine indicates that the feline subject that will benefit from the treatment. In some embodiments, the methods for identifying a feline subject that will benefit from such treatment to reduce the likelihood of developing calcium oxalate bladder stones comprise analyzing a sample from the feline subject to determine if the level of circulating 2-oxoarginine indicates that the feline subject that will benefit from the treatment.

Methods are provided for treating a feline subject to reduce the likelihood of developing calcium oxalate bladder stones. The treatment to reduce risk of calcium oxalate stone formation that comprises administering effective amounts of one or more of the components selected from the group consisting of betaine, green tea, fenugreek and tulsi. In some embodiments, the methods comprise administering effective amounts of one or more of the components selected from the group consisting of betaine, green tea, fenugreek and tulsi to a feline subject who has been identified as being a feline subject that will benefit from such treatment to reduce the likelihood of developing calcium oxalate bladder stones. In some embodiments, the methods comprise the steps of identifying a feline subject as being a feline subject that will benefit from such treatment to reduce the likelihood of developing calcium oxalate bladder stones and then administering effective amounts of one or more of the components selected from the group consisting of betaine, green tea, fenugreek and tulsi. A feline subject may be identified as being a feline subject that will benefit from such treatment to reduce the likelihood of developing calcium oxalate bladder stones by determining if the feline subject has a GG genotype for SNP A1_212891692 (felCat8) and/or determining if the level of circulating betaine indicates that the feline subject that will benefit from the treatment and/or determining a if the level of circulating 2-oxoarginine indicates that the feline subject that will benefit from the treatment.

Compositions are provided that comprise effective amounts of one or more of the components selected from the group consisting of betaine, green tea, fenugreek and tulsi. The compositions useful in the methods may be a cat food composition. Alternatively, effective amounts of one or more of the components selected from the group consisting of betaine, green tea, fenugreek and tulsi in may be administered as a supplement, a treat or toy or otherwise not incorporated into the food provided to the animal for daily nutritional intake.

As used herein, "an amount effective," "an effective amount," and like terms refer to that amount of one or more of betaine, green tea, fenugreek and tulsi effective to achieve a particular biological result, i.e., reduce the likelihood of developing calcium oxalate bladder stones. In specific embodiments, administration of an effective amount of a composition will be for a time sufficient to effect treatment. In a particular embodiment, the method comprises administration and consumption of a composition for a period of time sufficient to result in effective treatment and maintenance An effective amount may be based on several factors, including a cat's ideal weight, the age, gender, level of activity, the metabolizable energy of the composition, and the frequency of feeding the compositions, e.g., once, twice, or three times daily, and other compositions fed to the cat. In some embodiments an effective amount refers to an amount of one or more of betaine, green tea, fenugreek and tulsi administered so based upon total nutritional intake as a dry weight percentage A "food," "food composition," "pet food composition" or "cat food composition" can, in some embodiments, be a nutritionally complete diet for cat to which it is fed.

As used herein, an "ingredient" refers to any component of a composition.

The term "nutrient" refers to a substance that provides nourishment. In some cases, an ingredient may comprise more than one "nutrient," for example, a composition may comprise corn comprising important nutrients including both protein and carbohydrate.

Food compositions can be provided to in the form of cat food. A variety of commonly known types of cat foods are available to cat owners. The selection of cat food includes but is not limited to wet cat food, semi-moist cat food, dry cat food and cat treats. Wet cat food generally has a moisture content greater than about 65%. Semi-moist cat food typically has a moisture content between about 20% and about 65% and may include humectants, potassium sorbate, and other ingredients to prevent microbial growth (bacteria and mold). Dry cat food such as but not limited to food kibbles generally has a moisture content below about 15%. Pet treats typically may be semi-moist, chewable treats; dry treats in any number of forms, or baked, extruded or stamped treats; confection treats; or other kinds of treats as is known to one skilled in the art.

As used herein, the term "kibble" or "food kibble" refers to a particulate pellet like component of cat feeds. In some embodiments, a food kibble has a moisture, or water, content of less than 15% by weight. Food kibbles may range in texture from hard to soft. Food kibbles may range in internal structure from expanded to dense. Food kibbles may be formed by an extrusion process or a baking process. In non-limiting examples, a food kibble may have a uniform internal structure or a varied internal structure. For example, a food kibble may include a core and a coating to form a coated kibble. It should be understood that when the term "kibble" or "food kibble" is used, it can refer to an uncoated kibble or a coated kibble.

As used herein, the term "extrude" or "extrusion" refers to the process of sending preconditioned and/or prepared ingredient mixtures through an extruder. In some embodiments of extrusion, food kibbles are formed by an extrusion processes wherein a kibble dough, including a mixture of wet and dry ingredients, can be extruded under heat and pressure to form the food kibble. Any type of extruder can be used, examples of which include but are not limited to single screw extruders and twin-screw extruders. The list of sources, ingredients, and components as described hereinafter are listed such that combinations and mixtures thereof are also contemplated and within the scope herein.

As contemplated herein, compositions are meant to encompass, but not be limited to, nutritionally-complete and balanced cat food compositions. A "nutritionally complete diet" is a diet that includes sufficient nutrients for maintenance of normal health of a healthy cat on the diet. Nutritionally complete and balanced cat food compositions are familiar to one of skill in the art. For example, substances such as nutrients and ingredients suitable for nutritionally complete and balanced animal feed compositions, and recommended amounts thereof, may be found for example, in the Official Publication of the Association of American Feed Control Officials, Inc. (AAFCO), Atlanta, Ga., (2012).

It is contemplated that in feeding a cat a diet comprising an effective amount of amount of one or more of betaine, green tea, fenugreek and tulsi, a preferred method comprises feeding the cat a cat food that contains the betaine, green tea, fenugreek and/or tulsi as ingredients. In other embodiments, feeding a cat a diet comprising an effective amount of amount of one or more of betaine, green tea, fenugreek and tulsi is achieved by administering to the cat one or more of betaine, green tea, fenugreek and tulsi as a supplement or treat. Whether delivered in a cat food composition or as a separate supplement or in a treat, providing the cat with the effective amount of one or more of betaine, green tea, fenugreek and tulsi by any means is considered feeding a cat a diet comprising an effective amount of one or more of betaine, green tea, fenugreek and tulsi.

Betaine, which is also referred to as trimethylglycine is a modified amino acid consisting of glycine with three methyl groups.

In some embodiments, tulsi refers to the plant *Ocimum tenuiflorum* and derivatives thereof. Tulsi is also known as holy basil, tulasi, or thulasi. Tulsi is an aromatic perennial plant in the family Lamiaceae, native to the Indian subcontinent and widespread as a cultivated plant throughout the Southeast Asian tropics. By way of example, tulsi may include products derived from the leaves, stems, seeds, and roots of a tulsi plant. Tulsi may be in the form of a ground powder, freshly ground, spray dried, freeze dried, wet root, extract, oil, suspension, oil and water, or solution. The tulsi may be cooked or raw. Some of the phytochemical constituents of tulsi are oleanolic acid, ursolic acid, rosmarinic acid, eugenol, carvacrol, linalool, and β-caryophyllene. Tulsi essential oil consists mostly of eugenol, β-elemene, β-caryophyllene, and germacrene.

In some embodiments, the green tea originates from the plant species *Camellia sinensis*. Green tea is considered to have originated in China's Yunnan province Green tea considered an excellent source of antioxidants and alkaloids, containing vitamins, such as A, D, E, C, B, B5, H and K, manganese and other minerals such as zinc, chromium and selenium. Green tea is about 30 percent polyphenols by weight, including large amounts of a catechin EGCG. Catechins are natural antioxidants that are thought to help prevent cell damage.

In some embodiments, fenugreek refers to the plant *Trigonella foenum-graecum*, an annual plant in the family Fabaceae. Fenugreek is an annual plant cultivated worldwide as a semiarid crop. By way of example, fenugreek may include products derived from the leaves, stems, seeds, and roots of a fenugreek plant. Fenugreek may be in the form of a ground powder, freshly ground, spray dried, freeze dried, wet root, extract, oil, suspension, oil and water, or solution. Fenugreek may be cooked or raw. Fenugreek is used as a common spice, particularly in India and places that ingest curries. Traditional medicine practitioners have considered fenugreek to be useful for management of metabolic and nutritive disorders such as diabetes, as a phlegm mover, digestion promoter, labor inducer, and useful in breaking up stuck energies and cool inflammation.

As used herein, the term "supplement(s)" include, but are not limited to, a feed used with another feed to improve nutritive balance or performance of the total diet for an animal. Supplements include, but are not limited to, compositions that are fed undiluted as a supplement to other feeds, offered free choice with other parts of an animal's ration that are separately available, or diluted and mixed with an animal's regular feed to produce a complete feed. The AAFCO guidelines, for example, contain a discussion relating to supplements in the Official Publication of the Association of American Feed Control Officials, Inc. (AAFCO), Atlanta, Ga. (2012). Supplements may be in various forms including, for example, powders, liquids, syrups, pills, encapsulated compositions and the like.

Genetic Factors Indicating Responsiveness to Treatment for Reducing Risk

Genetic factors have been identified as being associated with a positive response to treatment to reduce the likelihood or risk of calcium oxalate stone formation in cats. Through a genome wide study of a feline colony, a single nucleotide polymorphism (SNP A1_212891692, felCat8; corresponding to SNP A1_212069607, felCat5), which is downstream from the AGXT2 gene, has been identified and associated with calcium oxalate stone formation in cats and whether or not effective treatment can be administered to reduce the risk. In particular, the presence of two copies of the major allele (the GG genotype) is associated with a beneficial response to certain treatments to reduce risk of calcium oxalate stone formation in cats. Cat with the GG genotype are particularly responsive to treatments described herein to reduce risk of calcium oxalate stone formation in cats.

A genome wide association analysis was performed which showed that there was a relationship between the AGXT2 (alanine-glyoxylate aminotransferase 2) gene and circulating concentrations of 2-oxoarginine, which is the product of the transamination of arginine. A relationship between AGXT2 polymorphism and circulating betaine levels has also been observed. The GG genotype is also associated with an increased concentration of circulating cytokines and other phenotypic traits that have detectable levels of biomarkers.

Cats with the GG genotype are responsive to a treatment to reduce risk of calcium oxalate stone formation that comprises administering one or more of the components selected from the group consisting of betaine, green tea, fenugreek and tulsi. Accordingly, determining the particular genotype of in the SNP A1_212891692 (felCat8), which is downstream of the feline AGTX2 gene, in a sample from a feline subject provides an accurate basis for determine whether or not the feline subject will benefit from such treatment.

Feline genetic polymorphism at SNP A1_212891692 can be used to identify a feline subject as either being a cat that will either benefit or not benefit from such treatment. A cat that has the GG genotype of SNP A1_212891692 will benefit from the treatment. The GG genotype, (also referred to as two-major allele genotype or the homozygous major allele genotype) refers to a cat having the major allele G present in both copies of SNP A1_212891692. Cats with either the AG genotype or the AA genotype are not cats that will benefit from the treatment. The AG genotype, (also referred to as major-minor allele genotype or the heterozygous genotype) refers to a cat having the major allele G present in one of the two copies of SNP A1_212891692 and the minor allele A present in the other of the two copies of SNP A1_212891692. The AA genotype, (also referred to as two-minor allele genotype or the homozygous minor allele genotype) refers to a cat having the minor allele A present in both copies of SNP A1_212891692.

The genotypic differences translate to detectable phenotypic differences. Cats that have the GG genotype have detectable differences circulating betaine and 2-oxoarginine levels compared to levels in cats that have the AA genotype or AG genotype. Biological samples from cats that have the GG genotype (the genotype that indicates a feline subject is a cat that will benefit from the treatment) have lower levels of betaine compared to the levels of betaine from biological samples from cats that have the AA genotype or AG genotype, i.e., the genotypes useful to identify a feline subject as not being a cat that will benefit from the treatment. Biological samples from cats that have the GG genotype (the genotype that indicates a feline subject is a cat that will benefit from the treatment) have higher levels of 2-oxoarginine compared to the levels of 2-oxoarginine from biological samples from cats that have the AA genotype or AG genotype, i.e., the genotypes useful to identify a feline subject as not being a cat that will benefit from the treatment.

Accordingly, in addition to or instead of determining genotype in order to identify a cat as being a cat that will benefit from the treatment to reduce risk of calcium oxalate stone formation or a cat that will not, these phenotypic differences can also be used to identify whether a feline subject is a cat that will benefit from the treatment to reduce risk of calcium oxalate stone formation or a cat that will not.

Genotypic analysis and one or more phenotypic analyses can be used individually, or in combination to provide confirmation and thus a higher level of accuracy in identifying a feline subject as either being a cat that will benefit from the treatment to reduce risk of calcium oxalate stone formation, wherein the treatment comprises administering one or more of the components selected from the group consisting of betaine, green tea, fenugreek and tulsi, or as being a cat that will not benefit from the treatment on the risk assessment, In some embodiments samples from a cat as analyzed for genotype. To identify a feline subject as a cat that will benefit from the treatment, one or more of the following analyses may be performed: genotypic analysis using a sample from the feline subject may be undertaken to determine that a feline subject has the GG genotype (the genotype that indicates a feline subject is a cat that will benefit from the treatment); the phenotypic analysis using a sample from the feline subject may be undertaken to identify betaine levels that indicate a feline subject is a cat that will benefit from the treatment; and the phenotypic analysis using a sample from the feline subject may be undertaken to identify 2-oxoarginine levels in a sample from the feline subject that indicate a feline subject is a cat that will benefit from the treatment. In some embodiments, only genotypic analysis is performed. In some embodiments, only analysis of betaine levels is performed. In some embodiments, only analysis of 2-oxoarginine levels is performed. In some embodiments, a combination of genotypic analysis and analysis of betaine levels is performed. In some embodiments, a combination of genotypic analysis and 2-oxoarginine levels is performed. In some embodiments, a combination of analysis of betaine levels and analysis of 2-oxoarginine levels is performed. In some embodiments, a combination of genotypic analysis, analysis of betaine levels and analysis of 2-oxoarginine levels is performed.

The treatment used to treat a feline subject identified as being a cat that will benefit from the treatment to reduce risk of calcium oxalate stone formation, wherein the treatment comprises administering one or more of the components selected from the group consisting of betaine, green tea, fenugreek and tulsi, comprises administering to the cat one or more ingredients selected from the group consisting of betaine, green tea, fenugreek and tulsi wherein the ingredients are incorporated to food used to feed the feline subject or administered as a supplement. Treatment using with one or more ingredients selected from the group consisting of betaine, green tea, fenugreek and tulsi can be used to prevent, reduce the likelihood, delay the onset or reduce the severity of calcium oxalate stones in cats identified as being a cat that will benefit from the treatment whether the feline subject is identified as such by detecting the GG genotype, decreased betaine levels or increased 2-oxoarginine levels. In some embodiments, the treatment comprises using with one, two, three or all four ingredients selected from the group consisting of betaine, green tea, fenugreek and tulsi two of betaine, green tea, fenugreek and tulsi.

Methods of treating cats to reduce the likelihood of developing calcium oxalate stones are provided that comprise identifying a feline subject as a cat that will benefit from the treatment and administering as part of a diet or by supplementation one or more of the components selected from the group consisting of betaine, green tea, fenugreek and tulsi. In some embodiments, treatment methods comprise the steps of: 1) either identifying a cat as a cat that would benefit by treatment that would reduce the likelihood of developing calcium oxalate stones and prevent, delay the onset or reduce the severity of calcium oxalate stones by one or more of a) genotypic analysis of SNP A1_212891692, and/or b) the phenotypic analysis to identify betaine levels indicative of an increased likelihood of developing calcium oxalate stones and/or c) the phenotypic analysis to identify 2-oxoarginine levels; and 2) administering as part of a diet or by supplementation one, two, three or preferably all four ingredients selected from the group consisting of betaine, green tea, fenugreek and tulsi in an effective amount. In some embodiments, compositions are administered as part of the cat's diet or administered in another manner. In some embodiments, cats are fed a diet that comprises ingredients or nutritional supplementation that includes one or more ingredients selected from the group consisting of betaine, green tea, fenugreek and tulsi. Preferred examples cats are fed a diet that that two, three or all four ingredients combined. In some embodiments, treatment comprises feeding the cat a diet supplemented with betaine, green tea, fenugreek and tulsi. In some embodiments, treatment comprises feeding the cat a diet supplemented with betaine, green tea, fenugreek and tulsi wherein the betaine is present in the range of 0.25% to 1.0% or 0.75% to 0.50%; the green tea is present in the range of 0.1% to 0.5%, or 0.20% to 0.30%, the fenugreek is present in the range of 0.01% to 0.05% or 0.020% to 0.030%, and the tulsi is present in the range of 0.0005% to 0.003% or 0.0010% to 0.002%. In some embodiments, treatment comprises feeding the cat a diet supplemented with 0.5% betaine, 0.25% green tea, 0.025% fenugreek and 0.0015% tulsi.

Kits, reagents, other articles, and compositions useful in methods for identifying a feline subject as either being a cat that will benefit from the treatment to reduce risk of calcium oxalate stone formation, wherein the treatment comprises administering one or more of the components selected from the group consisting of betaine, green tea, fenugreek and tulsi, or as not being a cat that will benefit from the treatment and methods of treating a feline subject as being a cat that will benefit from the treatment to reduce risk of calcium oxalate stone formation are provided. The kits, reagents, other articles, and compositions may be useful in methods that evaluate genotype and/or methods that evaluate betaine and/or 2-oxoarginine levels. Kits, reagents, other articles, and compositions useful in methods that evaluate betaine and/or 2-oxoarginine levels may comprise reagents useful in assays to measure such betaine and/or 2-oxoarginine levels and may also comprise positive control samples and negative control samples.

Kits, reagents, other articles, and compositions useful methods are provided for treating feline subjects to prevent, reduce the likelihood, delay the onset, and/or reduce the severity of calcium oxalate stone formation. The feline subjects may be identified as having an increased likelihood of developing calcium oxalate stones or as being likely to benefit from a treatment that reduces risk of calcium oxalate stone formation by methods various provided herein. The methods of treating feline subjects to prevent, reduce the likelihood, delay the onset, and/or reduce the severity of calcium oxalate stone formation may comprises administering to the feline subject a composition that comprises one or more of betaine, green tea, fenugreek and tulsi. Compositions such as nutritional supplements and food comprising components and ingredients used in such treatments.

SNP A1_212891692 in Reference Genome felCat8 (Formerly Referred to as SNP A1_212069607 in Reference Genome felCat5

SNP A1_212891692 refers to the SNP of the feline chromosome A1 sequence downstream of the AGXT2 gene listed in the feline reference genome felCat8. In that database, SNP A1_212891692 refers to Chromosome A1 Base Position 212891692. SNP A1_212891692 is located in a sequence downstream of the AGXT2 gene.

FelCat8 is an improved reference genome for cat that was re-assembled using new DNA sequence for cat. FelCat5 is a previous reference genome for cat. SNP A1_212891692 in reference genome felCat8 corresponds to the SNP formerly referred to as SNP A1_212069607 in reference genome felCat5. The sequence in felCat5 that includes the SNP is updated in felCat8. The felCat8 sequence is more complete.

SNP A1_212891692 refers to the SNP located on Chromosome A1 Base Position 212891692 in felCat8. (SNP A1_212891692 in felCat8 is SNP A1_212069607 in felCat5, which refers to felCat5 Chromosome A1 Base Position 212069607.)

SEQ ID NO:1 is the sequence in felCat8 that includes SNP A1_212891692. SEQ ID NO:1 is chrA1:212891592-212891792 in felCat8.

>felCat8_dna    range=chrA1:212891592-212891792
5'pad=0 3'pad=38 strand=+repeatMasking=none

```
SEQ ID NO: 1:
ATATGTTAGT ATCTCTACAT GTGGGAGAAC CAGATGTCAG              40

GTTCATGTAT GATACAGCAG GAAGAACACA GCACGGCCTT              80

TGAAGTATTC CTGTTTATAG [A/G]AATAATTCT TTCATATGCA         120

GGTACGTGTG TGTGTGTGTG TGTGTGTGTG TGTGTGTGTG             160

TGTGTATTTT ATAAAGGTAG CTACTCCTTA TTCATAGATA T           201
```

In SEQ ID NO:1, the SNP is at position 101 (of 201), which corresponds to Chromosome A1 at position 212891692. SEQ ID NO:1 contains 100 nucleotides 5' of the SNP and 100 nucleotides 3' of the SNP. The SNP at nucleotide 101 of SEQ ID NO:1, (position 212891692 of Chromosome A1 felCat8) is shown with the minor allele A and the major allele G as alternative nucleotides.

As used herein, when referencing the SNP that is the subject of the polymorphism and genotyping referred to herein, SNP A1_212891692 is intended to refer to the same SNP presented in felCat8 and felCat5 (SNP A1_212069607). In felCat8 the SNP is located at chromosome 1, position 212891692; in felCat5 the SNP is located at chromosome 1, position 212069607.

The presence two G alleles (the GG genotype) based upon SNP detection in an individual feline's genome can be used to identify a feline subject as being a cat that will benefit from the treatment to reduce risk of calcium oxalate stone formation, wherein the treatment comprises administering one or more of the components selected from the group consisting of betaine, green tea, fenugreek and tulsi. The presence one A allele and one G allele (the AG genotype) or the presence two A alleles (the AA genotype) based upon SNP detection in an individual feline's genome can be used to identify a feline subject as not being a cat that will benefit from the treatment.

A feline subject is identified as being a cat that will benefit from the treatment to reduce risk of calcium oxalate stone formation by genotyping results that indicate the feline subject has the GG genotype. To genotype a feline subject, in some embodiments, a sample from the feline subject can be interrogated for the presence of both the G allele and the A allele. Detection of the presence of the G allele and the absence of the A allele indicates the GG genotype. Detection of the presence of the G allele and the A allele indicates the AG genotype. Detection of the absence of the G allele and the presence of the A allele indicates the AA genotype. In some embodiments, a sample from the feline subject can be interrogated for the presence of the A allele only; thereby only indirectly determining whether a G allele is present. Detection of the absence of the A allele indicates the GG genotype. Detection of the presence of the G allele indicates the feline subject is either the GG genotype or the AG genotype.

A feline subject is identified as being a cat that will benefit from the treatment to reduce risk of calcium oxalate stone formation by interrogating a biological sample obtained from the feline subject for the presence of SNP A1_212891692 major allele G and SNP A1_212891692 minor allele A, thereby providing for determining the feline subject has the GG genotype, the AG genotype or the AA genotype. Alternatively, a biological sample obtained from the feline subject may be interrogated for the presence of two copies of a SNP A1_212891692 minor allele A only. In such instances, detecting zero copies of a SNP A1_212891692 minor allele A is an indirect detection of two Gs and thus the GG genotype. When only interrogating for minor allele A, the detection of presence of a minor allele A indicates that the feline subject has either the AA genotype or the AG genotype; in either case feline subject is identified as not being a cat that will benefit from the treatment. Thus, the analysis of the biological sample obtained from the feline subject for the presence of two copies of a SNP A1_212891692 major allele G can involve either using technology to directly detect the presence of major allele G and minor allele A, thereby providing the ability to directly identify the GG genotype, the AG genotype and the AA genotype. Alternatively, using technology to detect the presence or absence of minor allele A only provides the ability to indirectly detect the presence of GG genotype if zero minor allele As are detected.

One skilled in the art, using the coordinates disclosed in the sequence from the reference genome can determine the genotype of a subject. Methods of determining the genotype with respect to single nucleic acid polymorphism SNP A1_212891692 are provided. Those skilled in the art could, using the information provided herein, determine the genotype of an individual feline. In some embodiments, the sample used to perform the genotype analysis is a genomic DNA sample. In some embodiments, the sample is obtained from blood, saliva, follicle root, nasal swab or oral swab of the feline subject. In some embodiments, the biological sample is a genomic DNA sample obtained from the feline subject using the commercially available kit such as PER-FORMAgene PG-100 Oral sample collection it (DNA Genotek, OraSure Technologies, Inc., Bethlehem, Pa.). The preferred method for determining the presence or absence of specific alleles as a single SNP is a PCR based assay using an allele specific fluorescent probe to determine which variant(s) are present in the sample.

In some embodiments, genotype on an individual cat for SNP A1-212069607 may be determined using methods that include at least one nucleic acid analysis technique selected from: DNA sequencing, restriction enzyme digest, polymerase chain reaction (PCR), hybridization, real-time PCR, reverse transcriptase PCR, or ligase chain reaction.

In some embodiments, genotype on an individual cat for SNP A1-212069607 may be determined by performing at least one nucleic acid analysis technique selected from the group consisting of: analysis using a whole genome SNP chip; single-stranded conformational polymorphism (SSCP) assay; restriction fragment length polymorphism (RFLP); automated fluorescent sequencing; clamped denaturing gel electrophoresis (CDGE); denaturing gradient gel electrophoresis (DGGE); mobility shift analysis; restriction enzyme analysis; heteroduplex analysis; chemical mismatch cleavage (CMC); RNase protection assays; use of polypeptides that recognize nucleotide mismatches; allele-specific PCR; sequence analysis; and SNP genotyping.

In some embodiments, genotype on an individual cat for SNP A1-212069607 may be determined using a method selected from the types of methods consisting of: hybridization-based methods, enzyme-based methods, post-amplification methods based on physical properties of DNA, and sequencing methods.

In some embodiments, genotype on an individual cat for SNP A1-212069607 may be determined using a method selected from the types of methods consisting of: hybridization-based methods selected from the group consisting of: dynamic allele-specific hybridization, molecular beacon methods and SNP microarrays; enzyme-based methods selected from the group consisting of: restriction fragment length polymorphism (RFLP), PCR-based methods, Flap endonuclease, primer extension methods, 5'-nuclease and oligonucleotide ligation assay; post-amplification methods based on physical properties of DNA selected from the group consisting of: single strand conformation polymorphism, temperature gradient gel electrophoresis, denaturing high performance liquid chromatography, high-resolution amplicon melting, DNA mismatch-binding proteins, SNPlex, and surveyor nuclease assay; and sequencing methods In some embodiment, genotype on an individual cat for SNP A1-212069607 may be determined using a high-density array that contains genetic markers to interrogate SNP A1-212069607 for the presence of zero, one or two copies of the major and/or minor allele. In some embodiment, low-density array may be used. In some embodiment, in addition to interrogating the sample for the genotype with respect to SNP A1-212069607, other analyses and detections of SNPs may be performed using a high-density array containing genetic markers capable of detected a variety of SNPs.

Genotype analysis may be performed using hybridization-based methods. Examples of hybridization-based methods include dynamic allele-specific hybridization, methods that employ molecular beacons, and methods that employ SNP microarrays including high-density oligonucleotide SNP arrays or low-density oligonucleotide SNP arrays. SNPs can be interrogated by hybridizing complementary DNA probes to the SNP site. In dynamic allele-specific hybridization, a genomic segment is amplified and attached to a bead through a PCR reaction with a biotinylated primer. The amplified product is then attached to a streptavidin column and washed to remove the unbiotinylated strand. An allele-specific oligonucleotide is then added in the presence of a molecule that fluoresces when bound to double-stranded DNA. The intensity is measured as temperature is increased until the melting temperature (Tm) can be determined. SNP are detected by their lower than expected Tm. Specifically engineered single-stranded oligonucleotide probes are used in SNP detection that uses molecular beacons. Oligonucleotides are designed in which complementary regions are at each end and a probe sequence is located in between such that probe take on a hairpin, or stem-loop, structure in its natural, isolated state. A fluorophore is attached to one end of the probe a fluorescence quencher is attached to the other end. The fluorophore is in close proximity to the quencher when the oligo is in a hairpin configuration and the molecule does not emit fluorescence. The probe sequence is complementary to the genomic DNA used in the assay. If the probe sequence of the molecular beacon encounters its target genomic DNA during the assay, it will anneal and hybridize. The oligo will no longer assume the hairpin configuration and will fluoresce. High-density oligonucleotide SNP arrays comprise hundreds of thousands of probes arrayed on a small chip, allowing for many SNPs to be interrogated simultaneously. Several redundant probes designed to have the SNP site in several different locations as well as containing mismatches to the SNP allele are used to interrogate each SNP. The differential amount of hybridization of the target DNA to each of these redundant probes, allows for specific homozygous and heterozygous alleles to be determined.

Genotype analysis may be performed using enzyme-based methods. A broad range of enzymes including DNA ligase, DNA polymerase and nucleases may be employed. Examples of enzyme-based methods include methods based upon restriction fragment length polymorphism (RFLP), PCR-based methods, methods that utilize Flap endonuclease; methods that utilize primer extension, methods that utilize 5'-nuclease and methods that include oligonucleotide ligation assays. RFLP methods to detect SNPs use many different restriction endonucleases to digestion a genomic sample. It is possible to ascertain whether or not the enzymes cut the expected restriction sites by determining fragment lengths through a gel assay. RFLP assays are designed to include enzymes that cut in the presence or absence of SNPs and the pattern of fragment lengths can be used to determine the presence or absence of SNPs. PCR based methods include tetra-primer amplification refractory mutation system PCR, or ARMS-PCR, and multiple qPCR reactions. Tetra-primer amplification refractory mutation system PCR, or ARMS-PCR, employs two pairs of primers to amplify two alleles in one PCR reaction. The primers are designed such that the two primer pairs overlap at a SNP location but each match perfectly to only one of the possible SNPs. Alternatively, multiple qPCR reactions can be run with different primer sets that target each allele separately. Some embodiments utilize Flap endonuclease (FEN), which is an endonuclease that catalyzes structure-specific cleavage. This cleavage is highly sensitive to mismatches and can be used to interrogate SNPs with a high degree of specificity. A FEN called cleavase is combined with two specific oligonucleotide probes, that together with the target DNA, can form a tripartite structure recognized by cleavase. The first probe, called the Invader oligonucleotide is complementary to the 3' end of the target DNA. The last base of the Invader oligonucleotide is a non-matching base that overlaps the SNP nucleotide in the target DNA. The second probe is an allele-specific probe which is complementary to the 5' end of the target DNA, but also extends past the 3' side of the SNP nucleotide. The allele-specific probe will contain a base complementary to the SNP nucleotide.

Primer extension is a two-step process that first involves the hybridization of a probe to the bases immediately upstream of the SNP nucleotide followed by a 'mini-sequencing' reaction, in which DNA polymerase extends the hybridized primer by adding a base that is complementary to the SNP nucleotide. This incorporated base is detected and determines the SNP allele. The primer extension method is used in a number of assay formats. These formats use a wide range of detection techniques that include MALDI-TOF Mass spectrometry (see Sequenom) and ELISA-like methods. Sequenom's iPLEX SNP genotyping method, which uses a MassARRAY mass spectrometer. The flexibility and specificity of primer extension make it amenable to high throughput analysis. Primer extension probes can be arrayed on slides allowing for many SNPs to be genotyped at once. Referred to as arrayed primer extension (APEX), this technology has several benefits over methods based on differential hybridization of probes.

Several methods of genotype analysis are based upon DNA's physical properties such as melting temperature and single stranded conformation. Methods that use single stranded conformation are based upon single-stranded DNA (ssDNA) that folds into a tertiary structure. The conformation is sequence dependent and most single base pair mutations will alter the shape of the structure. When applied to a gel, the tertiary shape will determine the mobility of the ssDNA, providing a mechanism to differentiate between SNP alleles. This method first involves PCR amplification of the target DNA. The double-stranded PCR products are denatured using heat and formaldehyde to produce ssDNA. The ssDNA is applied to a non-denaturing electrophoresis gel and allowed to fold into a tertiary structure. Differences in DNA sequence will alter the tertiary conformation and be detected as a difference in the ssDNA strand mobility. Temperature gradient gel electrophoresis (TGGE) or temperature gradient capillary electrophoresis (TGCE) methods are based on the principle that partially denatured DNA is more restricted and travels slower in a gel or other porous material. In another method, denaturing high performance liquid chromatography (DHPLC) uses reversed-phase HPLC to interrogate SNPs. In DHPLC, the solid phase which has differential affinity for single and double-stranded DNA. Another method used is high-resolution melting of the entire amplicon. Use of DNA mismatch-binding proteins may also be used to detect SNPs. MutS protein from *Thermus aquaticus* binds different single nucleotide mismatches with different affinities and can be used in capillary electrophoresis to differentiate all six sets of mismatches. SNPlex is a proprietary genotyping platform sold by Applied Biosystems. Surveyor nuclease assay uses surveyor nuclease, a mismatch endonuclease enzyme that recognizes all base substitutions and small insertions/deletions (indels), and cleaves the 3' side of mismatched sites in both DNA strands. Sequencing technologies can also be used in SNP detection. Advances in sequencing technology allow SNP detection by sequencing more practical.

Genotyping by sequencing using next generation sequencing technologies has become a common practice. Genotyping by sequencing, also called GBS, is a method to discover single nucleotide polymorphisms (SNP) in order to perform genotyping studies, such as genome-wide association studies (GWAS). GBS uses restriction enzymes to reduce genome complexity and genotype multiple DNA samples. After digestion, PCR is performed to increase fragments pool and then GBS libraries are sequenced using next generation sequencing technologies. With the advancement of next generation sequencing technologies such as Illumina short read sequencing by synthesis and PacBio's single molecule real time sequencing it is becoming more feasible to do GBS. In the future, development of new technologies such as nanopore single molecule sequencing may allow whole genome sequencing/genotyping.

2-Oxoarginine Concentration

There is an association between the genotype of a cat at SNP A1_212891692 (felCat8) on chromosome 1 downstream from the downstream of the AGXT2 gene and concentration of 2-oxoarginine, a substrate from the enzymatic activity of AGXT2. In cats that have the homozygous major allele GG genotype, 2-oxoarginine levels are about 2.8 times the 2-oxoarginine levels in cats that have the homozygous minor allele AA genotype, and about 1.4 times the 2-oxoarginine levels in cats that have the heterozygous minor-major allele AG genotype. In the study reported in Example 1 below, which used a 445 cat cohort, the mean 2-oxoarginine levels in the group of cats with homozygous minor allele AA genotype was 0.4492, the mean 2-oxoarginine levels in the group of cats with heterozygous minor-major allele AG genotype was 0.9239, and the mean 2-oxoarginine levels in the group of cats with homozygous major allele GG genotype was 1.267. Using data from a larger population of cats may add further precision and further refine these data but predictions can be made using these available data.

A sample from a feline subject can be evaluated to determine 2-oxoarginine levels and the measured result can be compared to a positive 2-oxoarginine reference value representative of 2-oxoarginine levels of a cat that will benefit from the treatment. If the 2-oxoarginine levels in the feline subject's sample is equal to or greater than the positive 2-oxoarginine reference value, such results indicate that the feline subject as being a cat that will benefit from the treatment. If the 2-oxoarginine levels in the feline subject's sample is less than the positive 2-oxoarginine reference value, such results indicate that the feline subject as not being a cat that will benefit from the treatment. Methods of treating cats to reduce the likelihood of calcium oxalate stone formation could include the step of identifying a feline subject as being a cat that will benefit from the treatment by the method comparing the feline subject's 2-oxoarginine levels to positive 2-oxoarginine reference values that indicate a cat that will benefit from the treatment.

A feline subject can also be identified as not being a cat that will benefit from the treatment using a negative 2-oxoarginine reference value which representative of 2-oxoarginine levels of a cat that will not benefit from the treatment. A sample from a feline subject can be evaluated to determine 2-oxoarginine levels and the measured result can be compared to a negative 2-oxoarginine reference value. If the 2-oxoarginine levels in the feline subject's sample is equal to or less than the negative 2-oxoarginine reference value, such results indicate that the feline subject as not being a cat that will benefit from the treatment.

Data in Table 1 in Example 1 provide representative positive 2-oxoarginine reference values and negative 2-oxoarginine reference values. Different data from different studies may provide slightly different numbers but representative positive 2-oxoarginine reference values and negative 2-oxoarginine reference value are constant with respect to the calculations for any given cohort. Cumulative data generated by aggregating data provides more precise and accurate numerical representation of the representative positive 2-oxoarginine reference values and negative 2-oxoarginine reference value.

Alternatively, or additionally to methods that use a representative reference values as a reference for comparison to measured data from a feline subject, (positive and/or negative) control samples can be used to run (positive and/or negative) control assays.

A sample from a feline subject can be evaluated to determine 2-oxoarginine levels and the measured result can be compared to results obtained by measuring 2-oxoarginine levels in a 2-oxoarginine positive control sample that has 2-oxoarginine levels of a cat that will benefit from the treatment. Based upon these methods and the comparison step thereof, a cat may be identified as being a cat that will benefit from the treatment or as not being a cat that will benefit from the treatment. For example, if the sample from the feline subject sample that is compared with a 2-oxoarginine positive control sample and the results show that 2-oxoarginine levels in the feline subject are equal to or greater than the 2-oxoarginine levels in the 2-oxoarginine positive control sample, the feline subject would be identified as being a cat that will benefit from the treatment. On the other hand, if the sample from the feline subject sample that is compared with a 2-oxoarginine positive control sample and the results show that 2-oxoarginine levels in the feline subject are less than the 2-oxoarginine levels in the 2-oxoarginine positive control sample, the feline subject would be identified as not being a cat that will benefit from the treatment. Results of the identification methods may be used to inform treatment decisions. Methods of treating cats to reduce the likelihood of calcium oxalate stone formation could include the step of identifying a feline subject as being a cat that will benefit from the treatment by the method comparing measured 2-oxoarginine levels from the feline subject to measured 2-oxoarginine levels in a 2-oxoarginine positive control sample. A feline subject identified as being a cat that will benefit from the treatment by this method is then treated with the treatment.

A feline subject can also be identified as not being a cat that will benefit from the treatment using a 2-oxoarginine negative control sample that has 2-oxoarginine levels of a cat that will nor benefit from the treatment. A negative control assay could be performed to determine 2-oxoarginine levels in the 2-oxoarginine negative control sample. A sample from a feline subject can be evaluated to determine the feline subject's 2-oxoarginine levels which can be compared to the 2-oxoarginine levels in a 2-oxoarginine negative control sample. Based upon these methods and the comparison step thereof, a cat may be identified as not being a cat that will benefit from the treatment. For example, if the sample from the feline subject sample that is compared with a 2-oxoarginine negative control sample and the results show that 2-oxoarginine levels in the feline subject are equal to or less than the 2-oxoarginine levels in the 2-oxoarginine negative control sample, the feline subject would be identified as not being a cat that will benefit from the treatment.

Data in Table 1 in Example 1 provide representative positive 2-oxoarginine reference values and negative 2-oxoarginine reference values which can be used to create 2-oxoarginine positive control samples and 2-oxoarginine negative control samples. Different data from different studies may provide slightly different numbers but representative positive 2-oxoarginine reference values and negative 2-oxoarginine reference value are constant with respect to the calculations for any given cohort. Cumulative data generated by aggregating data provides more precise and accurate numerical representation of the representative positive 2-oxoarginine reference values and negative 2-oxoarginine reference value.

Betaine Concentration

There is an association between the genotype of a cat at SNP A1_212891692 (felCat8) on chromosome 1 downstream from the downstream of the AGXT2 gene and betaine concentrations. A significant difference in circulating betaine concentration has been observed when comparing circulating betaine levels in a cohort of cats made up of groups having the various genotypes.

Circulating betaine levels in cats that have the GG genotype (i.e. the genotype that indicates an increased likelihood of calcium oxalate stone formation) were observed to be about 18% lower than the circulating betaine levels in cats that have the AA genotype (i.e. the genotype that indicates a decreased likelihood of calcium oxalate stone formation). Circulating betaine levels in cats that have the heterozygous AG genotype (i.e. the genotype that indicates an intermediate likelihood of calcium oxalate stone formation) were observed to be about 9% lower than the circulating betaine levels in cats that have the homozygous minor allele AA genotype. Specifically, data from the study reported in Example 2 showed circulating betaine levels of 1.36, 1.24, 1.11 for genotypes AA, AG and GG, respectively. Using data from a larger population of cats may add further precision and further refine these data but predictions can be made using these available data.

A sample from a feline subject can be evaluated to determine betaine levels and the measured result can be compared to a positive betaine reference value representative of betaine levels of a cat that will benefit from the treatment. If the betaine levels in the feline subject's sample is equal to or less than the positive betaine reference value, such results indicate that the feline subject as being a cat that will benefit from the treatment. If the betaine levels in the feline subject's sample is greater than the positive betaine reference value, such results indicate that the feline subject as not being a cat that will benefit from the treatment. Methods of treating cats to reduce the likelihood of calcium oxalate stone formation could include the step of identifying a feline subject as being a cat that will benefit from the treatment by the method comparing the feline subject's betaine levels to positive betaine reference values that indicate a cat that will benefit from the treatment.

A feline subject can also be identified as not being a cat that will benefit from the treatment using a negative betaine reference value which representative of betaine levels of a cat that will not benefit from the treatment. A sample from a feline subject can be evaluated to determine betaine levels and the measured result can be compared to a negative betaine reference value. If the betaine levels in the feline subject's sample is equal to or greater than the negative betaine reference value, such results indicate that the feline subject as not being a cat that will benefit from the treatment.

Data in Table 2 in Example 2 provide representative positive betaine reference values and negative betaine reference values. Different data from different studies may provide slightly different numbers but representative positive betaine reference values and negative betaine reference value are constant with respect to the calculations for any given cohort. Cumulative data generated by aggregating data provides more precise and accurate numerical representation of the representative positive betaine reference values and negative betaine reference value.

Alternatively, or additionally to methods that use a representative reference values as a reference for comparison to measured data from a feline subject, (positive and/or negative) control samples can be used to run (positive and/or negative) control assays.

A sample from a feline subject can be evaluated to determine betaine levels and the measured result can be compared to results obtained by measuring betaine levels in a betaine positive control sample that has betaine levels of a cat that will benefit from the treatment. Based upon these methods and the comparison step thereof, a cat may be identified as being a cat that will benefit from the treatment or as not being a cat that will benefit from the treatment. For example, if the sample from the feline subject sample that is compared with a betaine positive control sample and the results show that betaine levels in the feline subject are equal to or less than the betaine levels in the betaine positive control sample, the feline subject would be identified as being a cat that will benefit from the treatment. On the other hand, if the sample from the feline subject sample that is compared with a betaine positive control sample and the results show that betaine levels in the feline subject are greater than the betaine levels in the betaine positive control sample, the feline subject would be identified as not being a cat that will benefit from the treatment. Results of the identification methods may be used to inform treatment decisions. Methods of treating cats to reduce the likelihood of calcium oxalate stone formation could include the step of identifying a feline subject as being a cat that will benefit from the treatment by the method comparing measured betaine levels from the feline subject to measured betaine levels in a betaine positive control sample. A feline subject identified as being a cat that will benefit from the treatment by this method is then treated with the treatment.

A feline subject can also be identified as not being a cat that will benefit from the treatment using a betaine negative control sample that has betaine levels of a cat that will nor benefit from the treatment. A negative control assay could be performed to determine betaine levels in the betaine negative control sample. A sample from a feline subject can be evaluated to determine the feline subject's betaine levels which can be compared to the betaine levels in a betaine negative control sample. Based upon these methods and the comparison step thereof, a cat may be identified as not being a cat that will benefit from the treatment. For example, if the sample from the feline subject sample that is compared with a betaine negative control sample and the results show that betaine levels in the feline subject are equal to or greater than the betaine levels in the betaine negative control sample, the feline subject would be identified as not being a cat that will benefit from the treatment.

Data in Table 2 in Example 2 provide representative positive betaine reference values and negative betaine reference values which can be used to create betaine positive control samples and betaine negative control samples. Different data from different studies may provide slightly different numbers but representative positive betaine reference values and negative betaine reference value are constant with respect to the calculations for any given cohort. Cumulative data generated by aggregating data provides more precise and accurate numerical representation of the representative positive betaine reference values and negative betaine reference value.

Compositions and Formulations

Application of the methodology outlined above has identified bioactive dietary components that have been combined to provide compositions, foods, and diets that provide significant benefits to cats identified that will benefit from a treatment to reduce the likelihood of calcium oxalate stone formation. The risk of calcium oxalate stone formation in feline subjects with the GG genotype can be significantly reduced by methods which lower 2-oxoarginine levels and/ or increase betaine levels such as methods which administer compositions that lower 2-oxoarginine levels and/or increase betaine levels. The risk of calcium oxalate stone formation in feline subjects with the GG genotype can be significantly reduced by methods which administer a composition comprising one or more of the following: betaine and botanicals such as green tea, fenugreek and tulsi. In some embodiments, the composition comprising one or more of the following: betaine and botanicals such as green tea, fenugreek and tulsi may be a supplement or preferably may be ingredients in the cat's diet. In some embodiments, two or more of betaine and botanicals such as green tea, fenugreek and tulsi are included. For example, combinations may include betaine and green tea, betaine and fenugreek, betaine and tulsi, green tea and fenugreek, green tea and tulsi, and fenugreek and tulsi. In some embodiments, the intervention comprises use of three or more of the following: betaine and botanicals such as green tea, fenugreek and tulsi. For example, combinations may include betaine, green tea and fenugreek, betaine, green tea and tulsi, and fenugreek, green tea and tulsi, and fenugreek and tulsi. In some embodiments, each of betaine and botanicals such as green tea, fenugreek and tulsi are used, preferable as food ingredients.

In some embodiments, the food product is a nutritionally complete diet for an adult feline. In a specific aspect, the food product is a nutritionally complete diet formulated for an adult companion feline.

In some embodiments, the compositions include food compositions that may comprise an effective amount of betaine, green tea, fenugreek and tulsi in combination with protein in an amount from 4% to 75% or more based on the total weight of the composition on a dry matter basis, fat in an amount from 5% to 50% or more based on the total weight of the composition on a dry matter basis, and carbohydrate from 5% to 75% or more based on the total weight of the composition on a dry matter basis, wherein the food composition is suitable for consumption by a cat.

The compositions, which are administered in methods provided herein, may be formulated as a food composition that, in certain embodiments, is a nutritionally-balanced and/or nutritionally-complete food product or diet. In other embodiments, the composition is formulated and prepared as a nutritional supplement, a treat, or a toy.

In some embodiments, for example, in addition to effective amounts of betaine, green tea, fenugreek and tulsi, a nutritionally complete and balanced cat food composition may comprise: from 4% to 90%, from 5% to 75%, from 10% to 60% protein, and from 15% to 50% by weight of protein; from 0% to 90%, from 2% to 80%, from 5% to 75%, and from 10% to 50% by weight of carbohydrate; from 2% to 60%, from 5% to 50%, and from 10% to 35% by weight of fat. The compositions may further contain from 0 to 15% or from 2% to 8%, by weight of vitamins and minerals, antioxidants, and other nutrients which support the nutritional needs of the animal.

Sources of proteins, carbohydrates, fats, vitamins, minerals, balancing agents, and the like, suitable for inclusion in the compositions, and particularly in the food products to be administered in methods provided herein, may be selected from among those conventional materials known to those of ordinary skill in the art.

In some embodiments, proteins useful as ingredients of the food compositions may comprise proteins from animal sources, such as animal proteins, including mammalian, avian protein, reptilian, amphibian, fish, invertebrate proteins and combinations thereof, e.g., from any of cattle, sheep, pig, goat, deer, rabbit, horse, kangaroo, their milk, curds, whey or blood, and internal tissues and organs such as smooth muscle, striate muscle, liver, kidney, intestine or heart; additional avian protein sources encompass turkey, goose, duck, ostrich, quail, pigeon, their eggs and internal tissues and organs such as smooth muscle, striate muscle, liver, kidney, intestine or heart; amphibian sources include frog or salamander, reptilian protein sources include alligator, lizard, turtle and snake; a fish protein sources include catfish, herring, salmon, tuna, bluefish, cod, halibut, trout, swordfish and their eggs; and an invertebrate protein sources include lobster, crab, clams, mussels or oysters, and combinations thereof, meat protein isolate, whey protein isolate, egg protein, mixtures thereof, and the like, as well as vegetable sources, such as soy protein isolate, corn gluten meal, wheat gluten, mixtures thereof, and the like.

In some embodiments, carbohydrates useful as ingredients of the food compositions may include but are not limited to, one or more of corn, whole yellow corn, grain sorghum, wheat, barley, rice, millet, brewers rice, oat groats, and polysaccharides (e.g., starches and dextrins) and sugars (e.g., sucrose, lactose, maltose, glucose, and fructose) that are metabolized for energy when hydrolyzed. Examples of additional carbohydrate sources suitable for inclusion in the compositions disclosed herein include, fruits and non-tomato pomace vegetables.

Fats useful as ingredients of the food compositions may be from any source, such as but not limited to poultry fat, beef tallow, lard, choice white grease, soybean oil, corn oil, canola oil, sunflower oil, mixtures thereof, and the like. The fat may be incorporated completely within the food composition, deposited on the outside of the food composition, or a mixture of the two methods.

In some embodiments, the compositions further include an effective amount of one or more substances selected from the group consisting of glucosamine, chondroitin, chondroitin sulfate, methylsulfonylmethane ("MSM"), creatine, antioxidants, *Perna canaliculata*, omega-3 fatty acids, omega-6 fatty acids and mixtures thereof.

In some embodiments, the food composition further comprises one or more amino acid such as but not limited to arginine, histidine, isoleucine, leucine, lysine, methionine (including DL-methionine, and L-methionine), phenylalanine, threonine, tryptophan, valine, taurine, carnitine, alanine, aspartate, cystine, glutamate, glutamine, glycine, proline, serine, tyrosine, and hydroxyproline.

In some embodiments, the food composition further comprises one or more fatty acids such as but not limited to lauric acid, myristic acid, palmitic acid, palmitoleic acid, margaric acid, margaroleic acid, stearic acid, oleic acid, linoleic acid, g-linolenic acid, a-linolenic acid, stearidonic acid, arachidic acid, gadoleic acid, DHGLA, arachidonic acid, eicossatetra acid, EPA, behenic acid, erucic acid, docosatetra acid, and DPA.

In some embodiments, the food composition further comprises one or more macro nutrients such as but not limited to moisture, protein, fat, crude fiber, ash, dietary fiber, soluble fiber, insoluble fiber, raffinose, and stachyose.

In some embodiments, the food composition further comprises one or more micro nutrients such as but not limited to beta-carotene, alpha-lipoic acid, glucosamine, chondroitin sulfate, lycopene, lutein, and quercetin.

In some embodiments, the food composition further comprises one or more minerals such as but not limited to calcium, phosphorus, potassium, sodium, chloride, iron, copper, copper, manganese, zinc, iodine, selenium, selenium, cobalt, sulfur, fluorine, chromium, boron, and oxalate.

In some embodiments, the food composition further comprises one or more other vitamins, such as but not limited to vitamin A, vitamin C, vitamin D, vitamin E, *quinoa* grain, thiamine, riboflavin, niacin, pyridoxine, pantothenic acid, folic acid, vitamin B 12, biotin, and choline.

In some embodiments, the food composition further comprises fiber, which may be supplied from a variety of sources, including, for example, vegetable fiber sources such as cellulose, beet pulp, peanut hulls, and soy fiber.

In some embodiments, the food composition further comprises stabilizing substances, for example, substances that tend to increase the shelf life of the composition. Potentially suitable examples of such substances include, for example, preservatives, antioxidants, synergists and sequestrants, packaging gases, stabilizers, emulsifiers, thickeners, gelling agents, and humectants. Examples of emulsifiers and/or thickening agents include, for example, gelatin, cellulose ethers, starch, starch esters, starch ethers, and modified starches.

In some embodiments, the food composition further comprises additives for coloring, palatability, and nutritional purposes include, for example, colorants; iron oxide, sodium chloride, potassium citrate, potassium chloride, and other edible salts; vitamins; minerals; and flavoring. The amount of such additives in a composition typically is up to 5% (dry basis of the composition).

Preparation of Compositions

The compositions that comprise betaine, green tea, fenugreek and tulsi may be prepared as food products suitable for consumption by cats. These food products may be of any consistency or moisture content; i.e., the compositions may be moist, semi-moist, or dry food products. "Moist" food products are generally those with a moisture content of from 60% to 90% or greater. "Dry" food products are generally those with a moisture content of from 3% to 11%, and are often manufactured in the form of small pieces or kibbles. "Semi-moist food products generally have a moisture content of from 25% to 35%. The food products may also include components of more than one consistency, for example, soft, chewy meat-like particles or pieces as well as kibble having an outer cereal component or coating and an inner "cream" component.

In some embodiments, the food products that comprise betaine, green tea, fenugreek and tulsi may be prepared in a canned or wet form using conventional food preparation processes known to those of ordinary skill in the art. Typically, ground animal proteinaceous tissues are mixed with the other ingredients, such as cereal grains, suitable carbohydrate sources, fats, oils, and balancing ingredients, including special purpose additives such as vitamin and mineral mixtures, inorganic salts, cellulose, beet pulp and the like, and water in an amount sufficient for processing. The ingredients are mixed in a vessel suitable for heating while blending the components. Heating the mixture is carried out using any suitable manner, for example, direct steam injection or using a vessel fitted with a heat exchanger. Following addition of all of the ingredients of the formulation, the mixture is heated to a temperature of from 50° F. to 212° F. Although temperatures outside this range can be used, they may be commercially-impractical without the use of other processing aids. When heated to the appropriate temperature, the material will typically be in the form of thick liquid, which is dispensed into cans. A lid is applied and the container is hermetically sealed. The sealed can is then placed in convention equipment designed for sterilization of the contents. Sterilization is usually accomplished by heating to temperatures of greater than 230° C. for an appropriate time depending on the temperature used, the nature of the composition, and related factors. The compositions and food products of the present invention can also be added to or combined with food compositions before, during, or after their preparation.

In some embodiments, the food products may be prepared in a dry form using convention processes known to those of ordinary skill in the art. Typically, dry ingredients, including dried animal protein, plant protein, grains and the like are ground and mixed together. Liquid or moist ingredients, including fats, oils water, animal protein, water, and the like are added combined with the dry materials. The specific formulation, order of addition, combination, and methods and equipment used to combine the various ingredients can be selected from those known in the art. For example, in certain embodiments, the resulting mixture is process into kibbles or similar dry pieces, which are formed using an extrusion process in which the mixture of dry and wet ingredients is subjected to mechanical work at high pressure and temperature, forced through small openings or apertures, and cut off into the kibbles, e.g., with a rotating knife. The resulting kibble can be dried and optionally coated with one or more topical coatings comprising, e.g., flavors, fats, oils, powdered ingredients, and the like. Kibbles may also be prepared from dough by baking, rather than extrusion, in which the dough is placed into a mold before dry-heat processing.

In preparing a composition, any ingredient generally may be incorporated into the composition during the processing of the formulation, e.g., during and/or after mixing of the other components of the composition. Distribution of these components into the composition can be accomplished by conventional means. In certain embodiments, ground animal and/or poultry proteinaceous tissues are mixed with other ingredients, including nutritional balancing agents, inorganic salts, and may further include cellulose, beet pulp, bulking agents and the like, along with sufficient water for processing.

In some embodiments, the compositions are formulated so as to be easier to chew. In specific embodiments, the compositions and food products are formulated to address specific nutritional differences between cats such as life stage, age, size, weight, body composition, and breed.

The compositions that comprise effective amounts of betaine, green tea, fenugreek and tulsi are formulated as a nutritionally complete diet to meet the needs of a mature adult feline. These nutritionally complete diets that include sufficient nutrients for maintenance of normal health of a healthy cat on the diet. Nutritionally complete and balanced cat food compositions are familiar to one of skill in the art. For example, substances such as nutrients and ingredients suitable for nutritionally complete and balanced animal feed compositions, and recommended amounts thereof, may be found for example, in the Official Publication of the Association of American Feed Control Officials, Inc. (AAFCO), Atlanta, Ga. (2012).

In another embodiment, treats comprising effective amounts of betaine, green tea, fenugreek and tulsi can be prepared by, for example, an extrusion or baking process similar to those described below for dry food to provide an edible product. Treats include, for example, compositions that are given to a cat to entice the cat to eat during a non-meal time. Treats may be nutritional, wherein the composition comprises one or more nutrients, and may, for example, have a composition as described above for food. Non-nutritional treats encompass any other treats that are non-toxic. Compositions can be coated onto the treat, incorporated into the treat, or both.

In another embodiment, an animal toy is provided that is a chewable or consumable toy. Such toys are typically prepared by coating any existing toy with effective amounts of betaine, green tea, fenugreek and tulsi. Toys therefore include, for example, chewable toys. In certain embodiments, the composition of the invention can form a coating on the surface of the toy or on the surface of a component of the toy, or it can be incorporated partially or fully throughout the toy, or both. A wide range of suitable toys are currently marketed. See, e.g., U.S. Pat. No. 5,339,771 (and references disclosed in U.S. Pat. No. 5,339,771). See also, e.g., U.S. Pat. No. 5,419,283 (and references disclosed in U.S. Pat. No. 5,419,283). It should be recognized that this invention contemplates both partially consumable and fully consumable toys.

All publications mentioned herein are incorporated by reference for the purpose of describing and disclosing the materials and methodologies that are reported in the publication, which might be used in connection with the invention.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

EXAMPLES

Example 1

A genome wide association study of a cohort of 445 cats was undertaken. Each of the 445 cats of the cohort was genotyped for the chromosome 1 SNP A1_212891692. The cats were divided into three groups based upon whether the genotype of the cat was homozygous minor allele AA (GROUP 11), heterozygous allele AG (GROUP 12) or homozygous major allele GG (GROUP 22). The frequency of each genotype in the cohort was calculated based upon the number of cats with each of the three genotypes. The level of metabolite 2-oxoarginine was measured for each cat and the mean level of metabolite 2-oxoarginine was determined for each cohort. Table 1 provides overview of study and data generated.

TABLE 1

| SNP | VALUE | GROUP 11 | GROUP 12 | GROUP 22 |
|---|---|---|---|---|
| A1_212069607 | Genotype | A/A | A/G | G/G |
| A1_212069607 | Number of animals with genotype | 30 | 169 | 230 |
| A1_212069607 | Frequency of genotype in cohort | 0.0699 | 0.3939 | 0.5361 |
| A1_212069607 | Mean level of 2-oxoarginine | 0.4492 | 0.9239 | 1.267 |

As shown in Table 1, of the 445 cats genotyped, about 7% (0.0699; 30/445) had the homozygous minor allele AA genotype; about 39% (0.3939; 169/445) had the heterozygous minor/major allele AG genotype; and about 54% (0.5361; 230/445) had the homozygous major allele GG genotype. As shown in Table 1, there is an association with the variant of AGXT2 and 2-oxoarginine (0.45, 0.91, 1.26 scaled data of AA, AG and GG respectively).

Example 2

A study was undertaken using 23 cats having various genotypes of the SNP A1_212891692 polymorphism. Nine cats had the AA genotype, four had the AG genotype and ten had the GG genotype.

Struvite stone risk analysis was completed on urinary samples by struvite relative super saturation (sRSS) assay. Calcium oxalate stone risk analysis was completed on urinary samples using COTT assay. Concurrently, urine was analyzed for relative sRSS using the EQUIL 2 program. In brief, this computer program calculates a urine supersaturation ratio (unitless) with respect to the common kidney stone components. The EQUIL 2 program provides an evaluation of the state of urinary saturation based on pH and total concentrations (M/L) of specific analytes.

Metabolomic analysis was completed by Metabolon® and scaled imputed data was used to compare specific genotypes. Sodium, potassium, calcium, magnesium, chloride, ammonium, citrate, phosphate, sulfate, and oxalate concentrations were measured. The method used thermodynamic stability constants to calculate free ion activities for urinary ions. These free ion activities were then used to calculate the supersaturation ratio of urine compared with what would form crystals in pure water.

An association between the SNP A1_212891692 polymorphism a circulating betaine levels was observed. Data reported in Table 2 below shows that circulating betaine levels were lowest in the group with the GG genotype and highest in the group with the AA genotype. Cats with the AG genotype had betaine levels between the levels found in the cats with the GG genotype and cats the AA genotype.

TABLE 2

| SNP | VALUE | Group AA | Group AG | Group GG |
|---|---|---|---|---|
| A1_212069607 | Genotype | A/A | A/G | G/G |
| A1_212069607 | Number of animals with genotype | 9 | 4 | 10 |
| A1_212069607 | Circulating betaine level | 1.36 | 1.24 | 1.11 |

Example 3

The interaction of the SNP A1_212891692 polymorphism and nutrition on calcium oxalate stone formation risk was evaluated using 23 cats. Calcium oxalate stone formation risk was measured using the COTT assay. In brief, the [Ca+2]/(added Ox-2) ratio is calculated (per liter). An increasing index value denotes samples at greater risk of calcium oxalate crystallization, whereas decreasing index values denotes those with less risk. The ratio represents the concentration of ionized calcium and the amount of oxalate that is added to initiate crystallization. Results from the COTT assay are predictive for incidence of calcium oxalate stone formation. A treatment that can lower COTT assay results indicates an effective treatment to reduce the likelihood of calcium oxalate stone formation. Data was also collected from sRSS assay to determine any effect on risk of struvite stone formation.

Calcium oxalate stone risk was evaluated to determine the effect of dietary inclusion of betaine, and botanicals (green tea, fenugreek and tulsi). Test Food contained betaine included at 0.5%, and botanicals green tea, fenugreek and tulsi, included at 0.25, 0.025 and 0.0015%, respectively. Control food was identical to Test food except Control food did not contain the additional components.

The experimental design was as follows. Days 1-28 were a "pre-feed period" in which all cats were placed on Control (non-enhanced) food for 28 days. During Days 29-56, cats were then separated into two groups: Group One was fed the Control food daily for the entire 28 days; Group Two was fed the Test food daily for the entire 28 days. During Days 57-84, the foods were switched: Group One was fed the Test food daily for the entire 28 days; Group Two was fed the Control food daily for the entire 28 days. Therefore, following the 28-day initial pre-feed period, each cat had after the next 56 days consumed the control food for 28 days and the enhanced food for 28 days. Urine and blood analyses were completed Day 28 (i.e. after the 28 days on the prefeed), at Day 56 (i.e. the 28-day mid-point immediately before foods were switched) and at Day 84, (i.e. the end of the 56-day test feeding period following prefeed).

Analysis of COTT values was on the natural logs of the COTT values as the COTT values were not normally distributed. The COTT analysis used the PROC MIXED analysis procedure in SAS using the 56-day period, the initial COTT values, cat age, day of test, food and genotype and their interactions in the model.

Data is shown in FIG. 1. COTT values for the subjects fed the control food were 2.66, 2.75, 2.72 for genotypes AA, AG and GG respectively. After consuming the Test food, the COTT values were 2.91, 2.39, 2.12 for genotypes AA, AG and GG respectively. Comparing COTT values when fed Test food versus when fed Control food, the Test Food had no significant influence on the COTT values for genotype AA. In contrast, comparing COTT values when fed Test food versus when fed Control food, for genotype GG the Test Food COTT values were significantly reduced compared to Control Food COTT value. Likewise, the COTT values for GG cats after feeding Test Food were significantly reduced compared to COTT values for AA cats after consuming Test food.

Accordingly, the effect of food on COTT values differed based on genotype. When the post-hoc means separation was completed the AA cats after eating the Test food had an increased COTT value when compared to the GG cats after eating the test food, and the GG cats had a decline in COTT values when eating the Test food compared to the COTT values of the GG cats after eating Control food. The GG genotype is sensitive to the food enhanced with betaine and botanicals (green tea, fenugreek and tulsi), significantly reducing the risk of calcium oxalate stone formation, while this same intervention is not at all effective in the changing the COTT value of the AA genotype. Data indicates the AG genotype is intermediate between the homozygous genotypes.

There was no change in sRSS with food. All mean values for sRSS were below 0.75 showing a very low risk for struvite stones.

Figure 2:
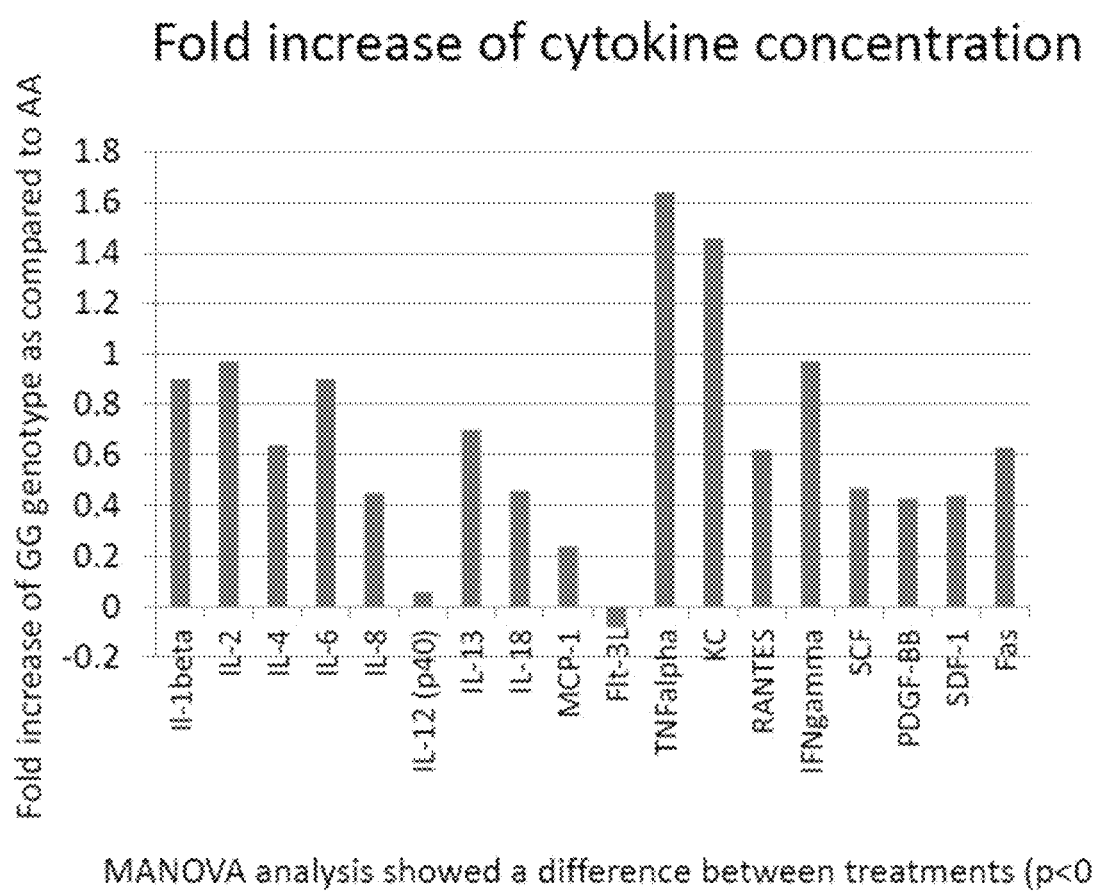
FIG. 2 shows the effect of food on COTT values differed based on genotype. Cats with the AA genotype had an increased COTT value after eating the enhanced food when compared to COTT values of cats with the GG genotype after eating the test food. Cats with the GG phenotype had a decline in COTT values when eating the enhanced food compared to the control.

Cytokine levels were also monitored. The cytokines were evaluated as a group by the PROC GLM MANOVA procedure in SAS. The Multivariant Anova procedure resulted in the conclusion (P<0.01) that the GG genotype has higher concentration of circulating cytokines that the AA genotype (FIG. 2). The GG genotype had an increased concentration of circulating cytokines.

Example 4

Blood is collected in order to determine plasma metabolomic profiles. Levels of 2-oxoarginine and/or betaine in plasma can be measured by a commercial laboratory (Metabolon, Durham, N.C., USA). Extracted supernatant is split and run on gas chromatography and liquid chromatography mass spectrometer platforms. The peak for each of 2-oxoarginine and betaine is known and the area under the peak for each sample can be normalized to a known sample. (See e.g. Evans, A. M., et al. (2009). Integrated, nontargeted ultrahigh performance liquid chromatography/electrospray ionization tandem mass spectrometry platform for the identification and relative quantification of the small-molecule complement of biological systems. Anal. Chem. 81, 6656-6667.) Gas chromatography (for hydrophobic molecules) and liquid chromatography (for hydrophilic molecules) are used to identify and provide relative quantification of metabolites such as 2-oxoarginine and/or betaine present in plasma samples. (See e.g.: Ballet, C. et al. (2018) New enzymatic and mass spectrometric methodology for the selective investigation of gut microbiota-derived metabolites, Chem. Sci., 9, 6233-6239; Akiyama, Y et al. (2012) A Metabolomic Approach to Clarifying the Effect of AST-120 on 5/6 Nephrectomized Rats by Capillary Electrophoresis with Mass Spectrometry (CE-MS) Toxins 2012, 4(11), 1309-1322; and Kikuchi K, et al. (2010) Metabolomic search for uremic toxins as indicators of the effect of an oral sorbent AST-120 by liquid chromatography/tandem mass spectrometry. J Chromatogr B Analyt Technol Biomed Life Sci 878:2997-3002.) Burrage, L C et al. (2019) Untargeted metabolomic profiling reveals multiple pathway perturbations and new clinical biomarkers in urea cycle disorders, Genetics in Medicine 21, 1977-1986 disclose analysis of plasma samples including measurement of 2-oxoarginine levels. Miller M J, et al. (2015) Untargeted metabolomic analysis for the clinical screening of inborn errors of metabolism. J Inherit Metab Dis. 38:1029-1039 and Kennedy A D, et al. (2016) Metabolomic profiling of human urine as a screen for multiple inborn errors of metabolism. Genet Test Mol Biomarkers. 20:485-495 also disclose technologies for measuring 2-oxoargine. Techniques may be adapted and used to measure 2-oxoarginine levels in samples from a feline subject. Midttun, O., et al. (2013). High-throughput, low-volume, multianalyte quantification of plasma metabolites related to one-carbon metabolism using HPLC-MS/MS. Anal Bioanal Chem 405, 2009-017, Fernandez-Roig, S., (2013) Low folate status enhances pregnancy changes in plasma betaine and dimethylglycine concentrations and the association between betaine and homocysteine. Am J Clin Nutr 97, 1252-59 and Holm, P. I., et al. (2005). Betaine and folate status as cooperative determinants of plasma homocysteine in humans. Arterioscler Thromb Vasc Biol 25, 379-385 disclose technologies for measuring betaine. Techniques may be adapted and used to measure betaine levels in samples from a feline subject.

Example 5

A saliva sample is obtained from a feline. The sample may be shipped as collected to a laboratory at another location, partially processed and then shipped to a laboratory at another location or completely processed and analyzed at a laboratory and the site of collection. If the sample is shipped as collected to a laboratory at another location or partially processed and then shipped to a laboratory at another location, results which may include some or all data collected from the sample by the laboratory may be transmitted to the site of collection and/or a veterinarian and/or the owner of or responsible party for the feline. After the saliva sample is obtained, it may be processed for analysis and evaluated for the presence of the GG genotype.

If results indicate that the feline will benefit from the treatments provided herein, the feline may be administering compositions comprising effective amounts of betaine and/or green tea and/or fenugreek and/or tulis.

Example 6

Samples are collected from felines using PERFORMAgene PG-100 Oral collection kit.

When doing so, the animal should not eat for 30 minutes or drink for 10 minutes before saliva collection, the individual doing the collection should not scrape the animal's teeth or cheek with the sponge nor should the animal be allowed to chew or bite the sponge.

The collection tube provided as part of the PERFORMAgene PG-100 Oral collection kit contains liquid that preserves the DNA sample and is required by the lab to analyze the sample. The cap should not be removed prior to sample collection.

In the first step of the collection protocol, the sponge is placed in the animal's mouth at the cheek pouch. Saliva is collected for 30 seconds by moving sponge and mopping saliva where it naturally pools (in the cheek pouch and under the tongue). For animals older than 6 months, moderate restraint may be required.

Next, holding the tube upright, the cap from the tube is unscrewed. The cap is turned upside down and the oral swab is placed in the tube. The cap is screwed on tightly to prevent liquid sample from leaking during transport. The tube is inverted and shaken vigorously numerous times, e.g. 10 times, to thoroughly mix sample.

A permanent marker may be used to clearly write the animal identification number on the white space available on the tube label.

The step-by-step laboratory protocol for manual purification of DNA from 0.5 mL aliquot of a Performagene™ sample that has been collected and preserved in Performagene chemistry with the PG-100 collection kit is as follows. The Reagents required for manual purification are available with PG-AC1 reagent package or PG-AC4 reagent package.

When a DNA sample is collected and mixed with the Performagene solution, the DNA is immediately stabilized Performagene samples are stable at room temperature for 1 year from the time of collection. Performagene samples can be stored indefinitely at −15° C. to −20° C., and can undergo multiple freeze-thaw cycles without deterioration of the DNA.

The following equipment and reagents are used in the purification process: a Microcentrifuge capable of running at 15,000×g; an air or water incubator at 50° C.; ethanol (95% to 100%) at room temperature; DNA buffer: TE (10 mM Tris-HCl, 1 mM EDTA, pH 8.0) or similar solution; optional glycogen (20 mg/mL) (e.g., Invitrogen Cat. No. 10814-010); ethanol (70%) at room temperature and 5M NaCl solution.

In the first step, the sample is mixed by shaking vigorously for 5 seconds. This is to ensure that viscous samples are properly mixed with the Performagene solution.

The sample is incubated in a 50° C. air incubator for a minimum of 2 hours, or in a 50° C. water incubator for a minimum of 1 hour. DNA in Performagene is stable at room temperature even without the incubation step. This heat-treatment step is essential to ensure that DNA is adequately released and that nucleases are permanently inactivated. This incubation step may be performed at any time after sample is collected from the animal and before it is purified. Incubation of the entire sample is recommended. The sample may be incubated at 50° C. overnight if it is more convenient. A longer time is required in an air incubator because temperature equilibration is slower than in a water incubator.

Optionally, the collection sponge may be removed. The cap is removed and the collection sponge is pressed against the inside of the tube to extract as much of the sample as possible. The sponge and cap are discarded. Sponge removal is dictated by preference of workflow.

Next, 500 µL of the mixed Performagene sample is transferred to a 1.5 mL microcentrifuge tube. The remainder of the Performagene sample can be stored at room temperature or frozen (−15° C. to −20° C.). 20 µL (1/25th volume) of PG-L2P purifier is then added to the microcentrifuge tube and mixed by vortexing for a few seconds. The sample becomes turbid as impurities and inhibitors are precipitated.

The sample is incubated on ice for 10 minutes (room temperature incubation can be substituted but will be slightly less effective in removing impurities) followed by centrifugation at room temperature for 5 minutes at 15,000× g. A longer period of centrifugation (up to 15 minutes) may be beneficial in reducing the turbidity (high A320) of the final DNA solution. The clear supernatant is transferred with a pipette tip into a fresh microcentrifuge tube and the pellet, which contains turbid impurities, is discarded. To 500 µL of supernatant, 25 µL (1/20$^{th}$ volume) of 5 M NaCl is added followed by mixing. The addition of NaCl is necessary to ensure efficient recovery of DNA. To 500 µL of supernatant, 600 µL of room temperature 95% to 100% ethanol is added followed by gentle mixing by inversion 10 times. During mixing with ethanol, the DNA will be precipitated. The DNA may appear as a clot of DNA fibers or as a fine precipitate, depending upon the amount of DNA in the sample. Even if no clot is seen, DNA will be recovered by carefully following the next steps.

The sample is allowed to stand at room temperature for 10 minutes to allow the DNA to fully precipitate. The tube is then placed in the centrifuge in a known orientation (DNA pellet may not be visible after centrifugation) and centrifuged at room temperature for 2 minutes at >15,000×g. For example, each tube may be placed in the microcentrifuge with the hinge portion of the cap pointing away from the center of the rotor. After centrifugation, the position of the pellet can be located (even if too small to be easily visible); it will be at the tip of the tube below the hinge.

The supernatant is removed with a pipette tip and discarded. The pellet contains DNA. Rotating the tube such that the pellet is on the upper wall will allow you to safely move a pipette tip along the lower wall and remove all of the supernatant. The supernatant may contain impurities and should be removed as completely as possible. Excessive drying of the pellet can make the DNA more difficult to dissolve. The DNA is washed by first adding 250 µL of 70% ethanol, then letting it stand for 1 minute at room temperature. The ethanol is removed with a pipette tip without disturbing the pellet. The 70% ethanol wash helps to remove residual inhibitors. Complete removal of ethanol, however, is essential to prevent inhibition during downstream applications. Therefore, the tube is centrifuged for 6 seconds to pool any remaining ethanol, which is removed with a pipette tip.

100 µL of DNA buffer (e.g. TE buffer) is added to the tube to dissolve the DNA pellet. Vortexing for at least 5 seconds aids in the dissolving process. To ensure complete rehydration of the DNA, let sit at room temperature overnight. DNA can now be quantified and used in downstream applications.

Assays that use fluorescent dyes are more specific than absorbance at 260 nm for quantifying the amount of double-stranded DNA (dsDNA) in a DNA sample. To quantify the DNA by fluorescence method, fluorescent dyes such as PicoGreen® or SYBR® Green I may be used to quantify dsDNA since there is less interference by contaminating RNA. Alternatively, commercially available kits such as Invitrogen's Quant-iT™ PicoGreen dsDNA Assay Kit (Cat. No. Q-33130) can be used. For either protocol, the purified DNA is preferably diluted 1:50 with TE solution and 5 µL is used in the quantification assay.

Alternatively, DNA may be quantified by absorbance in which case the purified sample is preferable first treated with RNase to digest contaminating RNA and then remove the RNA fragments by ethanol precipitation of the DNA. DNA from a Performagene sample typically contains appreciably more RNA than found in blood samples. Ensure that alcohol-precipitated DNA is fully dissolved before reading the absorbance. An absorbance of 1.0 at 260 nm corresponds to a concentration of 50 ng/µL (50 µg/mL) for pure dsDNA. A spectrophotometer cuvette capable of reading a volume of 100 µL or less should be used to avoid using too large a volume of sample. Absorbance values at 260 nm should be between 0.1 and 1.5. Lower values may not be reliable.

A 10 µL aliquot of purified RNase-treated DNA is diluted with 90 µL of TE (1/10 dilution) and mixed by gently pipetting up and down. Wait for bubbles to clear. TE is used in the reference (blank) cell. The absorbance is measured at 320 nm, 280 nm and 260 nm. Corrected $A_{280}$ and $A_{260}$ values are calculated by subtracting the absorbance at 320 nm ($A_{320}$) from $A_{280}$ and $A_{260}$ values. DNA concentration in ng/µL=corrected $A_{260}\times10$ (dilution factor)$\times50$ (conversion factor). $A_{260}/A_{280}$ ratio: divide corrected $A_{260}$ by corrected $A_{280}$.

Example 7

A daily diet that reduces the likelihood of calcium oxalate stones in cats identified as benefiting from a treatment that comprises betaine and the botanicals green tea, fenugreek and tulsi is provided. In some embodiments, methods may comprise feeding betaine and the botanicals green tea, fenugreek and tulsi to a cat identified as having the GG genotype of SNP A1_212891692. In some embodiments, methods may comprise feeding betaine and the botanicals green tea, fenugreek and tulsi to a cat identified as having 2-oxoarginine levels that are equal to or greater than a reference level corresponding to levels in cats identified as benefiting from a treatment and/or equal to or greater than levels measured in a positive control sample which contains 2-oxoarginine at a level corresponding to levels in cats identified as benefiting from a treatment. In some embodiments, methods may comprise feeding betaine and the botanicals green tea, fenugreek and tulsi to a cat identified as having betaine levels that are equal to or less than a reference level corresponding to levels in cats identified as benefiting from a treatment and/or equal to or less than levels measured in a positive control sample which contains betaine at a level corresponding to levels in cats identified as benefiting from a treatment. In some embodiments, methods may comprise analyzing a sample from a feline subject to determine if the feline subject has the GG genotype of SNP A1_212891692. In some embodiments, methods may comprise analyzing a sample from a feline subject to determine the level of 2-oxoarginine in the sample and comparing the measured level to either a reference level corresponding to a positive test result and/or the level measured in a positive control sample. In some embodiments, methods may comprise analyzing a sample from a feline subject to determine the level of betaine in the sample and comparing the measured level to either a reference level corresponding to a positive test result and/or the level measured in a positive control sample. The positive reference standard value corresponds to 2-oxoarginine or betaine levels deemed to be a positive result for a cat of comparable size, weight, age, breed inter alia.

Example 8

The following composition is based upon total nutrition to be provided per day. In some embodiments based on the total weight of the composition on a dry matter basis, the amount of betaine is equal to 0.25% to 1.0%, in some embodiments, 0.75% to 0.50% and in some embodiments about 0.50%. In some embodiments based on the total weight of the composition on a dry matter basis, the amount of green tea is equal to 0.1% to 0.5%. in some embodiments 0.20% to 0.30% and in some embodiments about 0.25%. In some embodiments based on the total weight of the composition on a dry matter basis, the amount of fenugreek is equal to 0.01% to 0.05%, in some embodiments, 0.020% to 0.030% and in some embodiments, about 0.025%. In some embodiments based on the total weight of the composition on a dry matter basis, the amount of tulsi is equal to 0.0005% to 0.003%, in some embodiments, 0.0010% to 0.002% and in some embodiments, 0.0015%. In certain embodiments, compositions may comprise chicken in an amount of 5%, 7.5%, 10%, 12.5%, 15%, 17.5%, 20%, 22.5% or 25% based on the total weight of the composition on a dry matter basis. In certain embodiments, compositions may comprise egg protein in an amount of 4%, 5%, 6%, 7%, 8%, 9%, 10%, 11%, 12%, 13%, 14% or 15% based on the total weight of the composition on a dry matter basis. In certain embodiments, compositions may comprise corn gluten meal in an amount of 6%, 7%, 8%, 9%, 10%, 11%, 12%, 13%, 14%, 15%, 16%, 17%, 18%, 19%, or 20% based on the total weight of the composition on a dry matter basis. In certain embodiments, compositions may comprise a vegetable source in an amount of 0.5%, 0.6%, 0.7%, 0.8%, 0.9%, 1.0%, 1.1%, 1.2%, 1.3%, 1.4%, 1.5%, 1.6%, 1.7%, 1.8%, or 1.9%, or 2.0% based on the total weight of the composition on a dry matter basis. In certain embodiments, compositions may comprise, in addition to tomato pomace, an additional fruit source in an amount of 0.1%, 0.2%, 0.3%, 0.4%, 0.5%, 0.6%, 0.7%, 0.8%, 0.9%, 1.0%, 1.1%, 1.2%, 1.3%, 1.4%, or 1.5% based on the total weight of the composition on a dry matter basis. In certain embodiments, compositions may comprise a carbohydrate selected from millet, brewers rice, oat groats, and combinations thereof in an amount of 5%, 10%, 15%, 20%, 25%, 30%, 35%, 40%, 45%, or 50% based on the total weight of the composition on a dry matter basis. In particular aspects of these embodiments, composition of the invention may comprise a dry weight of a carbohydrate source within a range defined by any two of these values as endpoints.

Example 9

Table 3 describes certain embodiments having proportion of the composition (% of dry weight of component composition)

TABLE 3

| | |
|---|---|
| Betaine | from about 0.25% to 1.0%, or from about 0.50% to 0.75%, or from about 0.50% |
| Green tea | from about 0.10% to 0.50%, or from about 0.20% to 0.30%, or from about 0.25% |
| fenugreek | from about 0.010% to 0.050%, or from about 0.020% to 0.030%, or from about 0.025% |
| tulsi | from about 0.0005% to 0.0030%, or from about 0.0010% to 0.0020%. or from about 0.0015% |
| Protein | from about 5% to about 70%, or from about 10% to about 70%, or from about 10% to about 60% |
| Carbohydrate (preferably a nitrogen-free or essentially nitrogen-free extract) | from about 0% to about 50%, or from about 5% to about 45% |
| Fat | from about 2% to about 50%, or from about 5% to about 50%, or from about 5% to about 40% |
| Dietary fiber | from about 0% to about 40%, or from about 1% to about 20%, or from about 1% to about 5.5% |
| Nutritional balancing agents (e.g., vitamins, and minerals) | from about 0% to about 15%, or from about 2% to about 8% |

Methods are provided that comprise feeding a cat a daily diet that comprises based on daily nutritional intake as the dry matter daily intake, 0.25% to 1.0% betaine, 0.1% to 0.5% green tea, 0.01% to 0.05% fenugreek and 0.0005% to 0.003% tulsi. In some embodiments, methods are provided that comprise feeding a cat a daily diet that comprises based on daily nutritional intake as the dry matter daily intake, 0.50% to 0.75% betaine, 0.2% to 0.3% green tea, 0.02% to 0.03% fenugreek and 0.0010% to 0.002% tulsi. In some embodiments, methods are provided that comprise feeding a cat a daily diet that comprises based on daily nutritional intake as the dry matter daily intake, about 0.50% betaine, about 0.25% green tea, about 0.025% fenugreek and about 0.0015% tulsi.

Example 10

Table 4 describes ingredients used in certain embodiments

TABLE 4

| Description | Content Range (Approx. w/w %) |
|---|---|
| Betaine | from about 0.25 to 1.0, or from about 0.75 to 0.50, or from about 0.50 |
| Green tea | from about 0.10 to 0.50, or from about 0.20 to 0.30, or from about 0.25 |
| fenugreek | from about 0.010 to 0.050, or from about 0.020 to 0.030, or from about 0.025 |
| tulsi | from about 0.0005 to 0.0030, or from about 0.0010 to 0.0020. or from about 0.0015 |
| Chicken, livers, hydrolyzed, dry | 25-45 |
| Hyvital ® wheat glutamine PN | 0.25-2 |
| Lysine, 1, hydrochloride | 0.1-0.75 |
| Methionine, dl | <0.08 |
| Taurine | 0.075-0.2 |
| Captex ® 355 Medium Chained Triglyceride | 1-5 |
| Cellulose, coarse | 1-5 |
| Beet, pulp | 1-3 |
| OatWell ® 22 oat bran | 2-5 |
| Pecan Fiber | 1-5 |
| MEG-3 ® 0355TG Fish Oil | 0.5-2.5 |
| Ginger Root Powder | 0.5-2 |
| Cranberry Pomace | 0.1-0.4 |
| Pomegranate Extract WS | 0.1-0.4 |
| Green Tea PE 50% EGCG WS | 0.1-0.4 |
| Boswellia PE 65% Boswellic Acids | 0.05-0.3 |
| Sensimune ™ 75 (Yeast Cell Wall) | 0.05-0.3 |

Example 11

Table 5 describes ingredients used in certain embodiments

TABLE 5

| Ingredient | Approx. w/w % |
|---|---|
| Betaine | from about 0.25 to 1.0, or from about 0.75 to 0.50, or from about 0.50 |
| Green tea | from about 0.10 to 0.50, or from about 0.20 to 0.30, or from about 0.25 |
| fenugreek | from about 0.010 to 0.050, or from about 0.020 to 0.030, or from about 0.025 |
| tulsi | from about 0.0005 to 0.0030, or from about 0.0010 to 0.0020. or from about 0.0015 |
| Chicken, livers, hydrolyzed, dry | up to 36.79 |
| Corn, starch, common canning | up to 32.45 |
| Choice White Grease | 1.00 |
| Mineral, premix, 2305 | 0.08 |
| Vitamin E, oil, 29% | 0.10 |
| Hyvital ® Wheat Glutamine PN | 1.00 |
| Lysine, 1, hydrochloride | 0.50 |
| Methionine, dl | 0.07 |
| Taurine | 0.10 |
| Captex ® 355 Medium Chained Triglyceride | up to 4.00 |
| Cellulose, coarse | up to 3.00 |
| Lactic acid, food grade | 1.50 |
| Dicalcium phosphate | 1.20 |
| Chicken, liver, digest, optimizor LDPE H | 2.00 |
| Sodium chloride, iodized | 0.40 |
| Choline chloride, liquid, 70% | 0.25 |
| Calcium carbonate | 2.00 |
| Potassium chloride | 0.70 |
| Beet, pulp | up to 2.50 |
| OatWell ® 22 oat bran | up to 3.00 |
| Pecan Fiber | up to 2.00 |
| MEG-3 ® 0355TG Fish Oil | 1.50 |
| Ginger Root Powder | 1.00 |
| Palatant | 0.75 |
| Natural flavor, Pork, Liver, Digest, D'T | 0.50 |
| Glyceryl monostearate | 0.25 |
| Cranberry Pomace | 0.20 |
| Pomegranate Extract WS | 0.20 |
| Green Tea PE 50% EGCG WS | 0.20 |
| Boswellia PE 65% Boswellic Acids | 0.20 |
| Sensimune ™ 75 (Yeast Cell Wall) | 0.15 |

Example 12

Table 6 describes ingredients used in certain embodiments

TABLE 6

| Ingredient | Approx. w/w % |
|---|---|
| Betaine | from about 0.25 to 1.0, or from about 0.75 to 0.50, or from about 0.50 |
| Green tea | from about 0.10 to 0.50, or from about 0.20 to 0.30, or from about 0.25 |
| fenugreek | from about 0.010 to 0.050, or from about 0.020 to 0.030, or from about 0.025 |
| tulsi | from about 0.0005 to 0.0030, or from about 0.0010 to 0.0020. or from about 0.0015 |
| Rice, brewers | up to 25.00 |
| Pea, protein concentrate | 10.00 |
| Chicken Dried 10% Ash | 8.00 |
| Chicken, ground, fresh | 7.00 |
| Sorghum, whole | 6.36 |
| Chicken Meal | 6.14 |
| Pork Fat, Choice White Grease | 1.00 |
| Flax, seed, whole | 3.00 |
| Eggs, dried, granulated | 5.50 |
| Pecan Fiber | 4.80 |
| G03 Buckwheat Groats | 4.00 |
| Oat, groats | 4.00 |
| Captex 355 Medium Chained Triglyceride | 3.00 |
| Chicken, liver, digest, optimizor LDPE H | 2.00 |
| Oat, fiber | 1.50 |
| Beet, pulp, ground, fine | 1.50 |
| Lactic acid, food grade | 1.50 |
| Fish oil, TG, 18/12, NP | 1.20 |
| Flay Gen#1 + CWG | 1.00 |
| Potassium chloride | 0.30 |
| Carnitine, 1, 10% | 0.27 |
| Natural flavor, Pork, Liver, Digest, D'T | 0.25 |
| Choline chloride, liquid, 70% | 0.18 |
| Sensimune 75 (Yeast Cell Wall) | 0.15 |
| Vitamin E, oil, 29% | 0.14 |
| Taurine | 0.10 |
| Sodium chloride, iodized | 0.10 |
| Lysine, 1, hydrochloride | 0.10 |
| Mineral, premix, 2305 | 0.04 |
| Oat Fiber, Fruit, Vegetable blend | 0.04 |
| Dicalcium phosphate | 0.04 |

Example 13

Table 7 describes ingredients used in certain embodiments

TABLE 7

| Ingredient | Approx. w/w % |
|---|---|
| Betaine | from about 0.25 to 1.0, or from about 0.75 to 0.50, or from about 0.50 |
| Green tea | from about 0.10 to 0.50, or from about 0.20 to 0.30, or from about 0.25 |
| fenugreek | from about 0.010 to 0.050, or from about 0.020 to 0.030, or from about 0.025 |
| tulsi | from about 0.0005 to 0.0030, or from about 0.0010 to 0.0020. or from about 0.0015 |
| Rice, Brewers | — |
| Chicken Meal | 7.00 |
| Pea, protein concentrate | 8.00 |
| Cellulose, coarse | 4.00 |
| Chicken Dried 10% Ash | 6.00 |
| Barley, pearled, cracked | up to 20.00 |
| Chicken, ground, fresh | 8.00 |
| Flax, seed, whole | 2.00 |
| Coconut oil preserved | 4.00 |
| Chicken, liver, digest, optimizor LDPE H | 3.00 |
| Lactic acid | 1.50 |
| Methionine, dl | 0.64 |
| Potassium chloride | 0.50 |
| Sodium chloride, iodized | 0.60 |
| Fish oil, TG, 18/12, NP | 0.50 |
| Calcium carbonate | 0.30 |
| Choline chloride, liquid, 70% | 0.25 |
| Carnitine, 1, 10% | 0.30 |
| Vitamin E, oil, 29% | 0.17 |
| Mineral, premix, 2305 | 0.08 |
| Taurine | 0.06 |
| Oat, groats | 10.00 |
| Buckwheat Groats | 6.92 |
| Pea, bran, meal | 5.00 |
| Tomato, pomace, | 5.00 |
| Beet, pulp, ground, fine | 3.00 |

Example 14

Table 8 describes ingredients used in certain embodiments

TABLE 8

| Ingredient | Approx. w/w % | Approx. w/w % |
|---|---|---|
| Betaine | from about 0.25 to 1.0, or from about 0.75 to 0.50, or from about 0.50 | from about 0.25 to 1.0, or from about 0.75 to 0.50, or from about 0.50 |
| Green tea | from about 0.10 to 0.50, or from about 0.20 to 0.30, or from about 0.25 | from about 0.10 to 0.50, or from about 0.20 to 0.30, or from about 0.25 |
| fenugreek | from about 0.010 to 0.050, or from about 0.020 to 0.030, or from about 0.025 | from about 0.010 to 0.050, or from about 0.020 to 0.030, or from about 0.025 |
| tulsi | from about 0.0005 to 0.0030, or from about 0.0010 to 0.0020. or from about 0.0015 | from about 0.0005 to 0.0030, or from about 0.0010 to 0.0020. or from about 0.0015 |
| Corn starch | 31.10 | 48.11 |
| Hydrolyzed chicken liver and heart | 37.00 | 32.00 |
| Soybean oil, crude, degummed | 3.60 | 4.66 |
| Cellulose, pelleted | — | 3.94 |
| Chicken, liver, digest, optimizer LDPE H | 2.00 | 2.00 |

TABLE 8-continued

| Ingredient | Approx. w/w % | Approx. w/w % |
|---|---|---|
| Lactic acid, food grade | 1.50 | 1.50 |
| Calcium carbonate | 1.22 | 1.22 |
| Dicalcium phosphate | 1.22 | 1.22 |
| Choice White Grease/Phos Acid | 1.25 | 1.00 |
| Flay Gen#1 + CWG | 1.25 | 0.75 |
| Glyceryl monostearate | 0.74 | 0.74 |
| Potassium chloride | 0.69 | 0.69 |
| Natural flavor, Pork, Liver, Digest, D'T | 0.75 | 0.50 |
| Sodium chloride, iodized | 0.44 | 0.44 |
| Choline chloride, liquid, 70% | 0.38 | 0.38 |
| Methionine, dl | 0.30 | 0.30 |
| Sodium tripolyphosphate | 0.15 | 0.15 |
| Vitamin premix | 0.12 | 0.12 |
| Mineral, premix, 2305 | 0.07 | 0.07 |
| Taurine | 0.02 | 0.02 |
| Pecan shells, ground | up to 7.00 | — |
| Flax seed whole brown | up to 3.00 | — |
| Beet pulp, ground, fine | up to 2.50 | — |
| Cranberry pomace | up to 1.00 | — |

Example 15

Table 9 describes ingredients used in certain embodiments

TABLE 9

| Ingredient | Approx. w/w % | Approx. w/w % |
|---|---|---|
| Betaine | from about 0.25 to 1.0, or from about 0.75 to 0.50, or from about 0.50 | from about 0.25 to 1.0, or from about 0.75 to 0.50, or from about 0.50 |
| Green tea | from about 0.10 to 0.50, or from about 0.20 to 0.30, or from about 0.25 | from about 0.10 to 0.50, or from about 0.20 to 0.30, or from about 0.25 |
| fenugreek | from about 0.010 to 0.050, or from about 0.020 to 0.030, or from about 0.025 | from about 0.010 to 0.050, or from about 0.020 to 0.030, or from about 0.025 |
| tulsi | from about 0.0005 to 0.0030, or from about 0.0010 to 0.0020. or from about 0.0015 | from about 0.0005 to 0.0030, or from about 0.0010 to 0.0020. or from about 0.0015 |
| Chicken meal | 15.36 | 15.36 |
| Rice, brewers | 8.64 | 8.64 |
| Eggs, dried, granulated | 8.00 | 8.00 |
| Corn, gluten, meal | 7.62 | 7.62 |
| Sorghum, whole | 5.00 | 5.00 |
| Choice white grease/Phos Acid | 4.00 | 4.00 |
| Palatant, 12 L, Liquid | 3.00 | 3.00 |
| Lactic acid, food grade | 1.50 | 1.50 |
| Soybean oil, crude, degummed | 1.05 | 1.05 |
| Palatant, ITE2, Dry | 1.00 | 1.00 |
| Potassium chloride | 0.89 | 0.89 |
| Sodium chloride, iodized | 0.61 | 0.61 |
| Calcium carbonate | 0.41 | 0.41 |
| Dicalcium phosphate | 0.25 | 0.25 |
| Vitamin E, oil, 29% | 0.17 | 0.17 |
| Choline chloride, liquid, 70% | 0.16 | 0.16 |
| Mineral, premix, 2305 | 0.06 | 0.06 |
| Tryptophan | 0.04 | 0.04 |
| Taurine | 0.04 | 0.04 |
| Cellulose, pelleted | — | 1.50 |
| Corn, yellow, whole | up to 26.00 | up to 40.00 |
| Pecan shells, ground | 7.00 | — |
| Flax seed whole brown | 3.00 | — |
| Beet pulp, ground, fine | 2.50 | 0.50 |
| Cranberry pomace | 1.00 | — |

Example 16

Table 10 describes ingredients used in certain embodiments

TABLE 10

| Ingredient | Approx. w/w % | Approx. w/w % | Approx. w/w % | Approx. w/w % |
|---|---|---|---|---|
| Betaine | 0.25 to 1.0, or 0.75 to 0.50, or 0.50 | 0.25 to 1.0, or 0.75 to 0.50, or 0.50 | 0.25 to 1.0, or 0.75 to 0.50, or 0.50 | 0.25 to 1.0, or 0.75 to 0.50, or 0.50 |
| Green tea | 0.10 to 0.50, or 0.20 to 0.30, or 0.25 | 0.10 to 0.50, or 0.20 to 0.30, or 0.25 | 0.10 to 0.50, or 0.20 to 0.30, or 0.25 | 0.10 to 0.50, or 0.20 to 0.30, or 0.25 |
| fenugreek | 0.010 to 0.050, or 0.020 to 0.030, or 0.025 | 0.010 to 0.050, or 0.020 to 0.030, or 0.025 | 0.010 to 0.050, or 0.020 to 0.030, or 0.025 | 0.010 to 0.050, or 0.020 to 0.030, or 0.025 |
| tulsi | 0.0005 to 0.0030, or 0.0010 to 0.0020. or 0.0015 | 0.0005 to 0.0030, or 0.0010 to 0.0020. or 0.0015 | 0.0005 to 0.0030, or 0.0010 to 0.0020. or 0.0015 | 0.0005 to 0.0030, or 0.0010 to 0.0020. or 0.0015 |
| Protein | 19.7-21.7 | 24.7-26.7 | 24.8-26.8 | 24.8-26.8 |
| Fat | 20.6-22.6 | 16.9-18.9 | 22.0-24.0 | 22.0-24.00 |
| Carbohydrate | 53.8-55.8 | 51.0-53.0 | 46.3-48.3 | 27.6-29.6 |
| Crude Fiber | 0.37-2.37 | 2.6-4.6 | 1.4-3.4 | 21.0-23.0 |

The invention claimed is:

1. A feline food composition comprising an amount of betaine that is equal to 0.1-1.0% of nutritional intake per day, an amount of green tea that is equal to 0.05-0.50% of nutritional intake per day, an amount of fenugreek that is equal to 0.005% to 0.1%, and an amount of tulsi that is equal to 0.0001-0.005%, wherein the composition reduces risk of calcium oxalate stone formation in a feline after administration of the feline food composition to the feline.

2. The feline food composition of claim 1 wherein the feline subject is fed a nutritional composition that comprises 0.25-1.0% betaine and/or 0.20-0.30% green tea and/or 0.01% to 0.05% fenugreek and/or 0.0005-0.003% tulsi.

3. The feline food composition of claim 1 comprising an amount of betaine that is equal to 0.25-1.0% of nutritional intake per day and an amount of green tea that is equal to 0.20-0.30% of nutritional intake per day and an amount of fenugreek that is equal to 0.01% to 0.05% and an amount of tulsi that is equal to 0.0005-0.003%.

4. The feline food composition of claim 1 comprising an amount of betaine that is equal to 0.50-0.75% of nutritional intake per day and/or an amount of green tea that is equal to 0.10-0.50% of nutritional intake per day and/or an amount of fenugreek that is equal to 0.02% to 0.03% and/or an amount of tulsi that is equal to 0.0010% to 0.002%.

5. The feline food composition of claim 1 comprising an amount of betaine that is equal to 0.50-0.75% of nutritional intake per day and an amount of green tea that is equal to 0.10-0.50% of nutritional intake per day and an amount of fenugreek that is equal to 0.02% to 0.03% and an amount of tulsi that is equal to 0.0010% to 0.002%.

6. The feline food composition of claim 1 comprising an amount of betaine that is equal to about 0.50% of nutritional intake per day and/or an amount of green tea that is equal to about 0.25% of nutritional intake per day and/or an amount of fenugreek that is equal to about 0.025% and/or an amount of tulsi that is equal to about 0.0015%.

7. The feline food composition of claim 1 comprising an amount of betaine that is equal to about 0.50% of nutritional intake per day and an amount of green tea that is equal to about 0.25% of nutritional intake per day and an amount of fenugreek that is equal to about 0.025% and an amount of tulsi that is equal to about 0.0015%.

8. The feline food composition of claim 1 further comprising:
a botanical complex, wherein the botanical complex comprises the green tea, the fenugreek, and the tulsi;

wherein the weight ratio of the betaine to the botanical complex is from about 2:1 to about 1:1.

9. The feline food composition according to claim 8, wherein the weight ratio of green tea to fenugreek is from about 5:1 to about 15:1.

10. The feline food composition according to claim 9, wherein the weight ratio of green tea to fenugreek is about 10:1.

11. A method of reducing risk of calcium oxalate stone formation in a feline subject comprising the steps of:
   identifying the feline subject as being a feline subject that would benefit from a treatment that reduces risk of calcium oxalate stone formation; and
   administering to the feline subject a composition that comprises effective amounts of betaine, green tea, fenugreek and tulsi
   wherein the composition comprises 0.1 to 1.0% betaine, 0.05 to 0.50% green tea, 0.005% to 0.1% fenugreek, and 0.0001 to 0.005% tulsi.

12. The method of claim 11, wherein identifying the feline subject that would benefit from the treatment that reduces risk of calcium oxalate stone formation comprises:
   analyzing a biological sample obtained from the feline subject for the presence of two copies of major allele G of SNP A1_212891692;
   wherein the presence of two copies of the major allele G of SNP A1_212891692 indicates that the feline subject would benefit from the treatment.

13. A method of identifying a feline subject that would benefit from a treatment that reduces risk of calcium oxalate stone formation, wherein the treatment that reduces risk of calcium oxalate stone formation comprises administering to the feline subject a composition that comprises an effective amount of betaine, green tea, fenugreek and tulsi, wherein the composition comprises 0.1 to 1.0% betaine, 0.05 to 0.50% green tea, 0.005% to 0.1% fenugreek, and 0.0001 to 0.005% tulsi; the method comprises
   analyzing a biological sample obtained from the feline subject for the presence of two copies of major allele G of SNP A1_212891692;
   wherein the presence of two copies of the major allele G of SNP A1_212891692 indicates that the feline subject would benefit from the treatment.

14. The method of claim 13, wherein the sample is a genomic DNA sample.

15. The method of claim 13, wherein the sample is obtained from blood, saliva, follicle root, nasal swab or oral swab of the feline subject, preferably saliva.

16. The method of claim 13, wherein the sample is analyzed by performing at least one nucleic acid analysis technique selected from: DNA sequencing, restriction enzyme digest, polymerase chain reaction (PCR), hybridization, real-time PCR, reverse transcriptase PCR, or ligase chain reaction.

17. The method of claim 13, wherein the sample is analyzed by performing at least one nucleic acid analysis technique selected from: analysis using a whole genome SNP chip, single-stranded conformational polymorphism (SSCP) assay, restriction fragment length polymorphism (RFLP), automated fluorescent sequencing; clamped denaturing gel electrophoresis (CDGE); denaturing gradient gel electrophoresis (DGGE), mobility shift analysis, restriction enzyme analysis, heteroduplex analysis, chemical mismatch cleavage (CMC), RNase protection assays, use of polypeptides that recognize nucleotide mismatches, allele-specific PCR, sequence analysis, and SNP genotyping.

18. The method of claim 13, wherein the sample is analyzed by performing at least one nucleic acid analysis technique selected from: hybridization-based methods, enzyme-based methods, post-amplification methods based on physical properties of DNA, and sequencing methods.

19. The method of claim 13, wherein the sample is analyzed by performing at least one nucleic acid analysis technique selected from: hybridization-based methods selected from the group consisting of dynamic allele-specific hybridization, molecular beacon methods and SNP microarrays; enzyme-based methods selected from the group consisting of restriction fragment length polymorphism (RFLP), PCR-based methods, Flap endonuclease, primer extension methods, 5'- nuclease and oligonucleotide ligation assay; post-amplification methods based on physical properties of DNA selected from the group consisting of single strand conformation polymorphism, temperature gradient gel electrophoresis, denaturing high performance liquid chromatography, high-resolution amplicon melting, DNA mismatch-binding proteins, SNPlex, and surveyor nuclease assay; and sequencing methods.

20. The method of claim 13, further comprising
   analyzing a biological sample obtained from the feline subject to determine the feline subject's betaine concentration; and
   comparing the feline subject's betaine concentration with a positive reference betaine concentration value that is representative of betaine concentration of a cat that would benefit from the treatment, wherein the feline subject's betaine concentration being equal to or less than the positive reference betaine concentration value indicates that the feline subject would benefit from a treatment.

21. The method of claim 13, further comprising
   analyzing a biological sample obtained from the feline subject to determine the feline subject's betaine concentration;
   analyzing a positive control sample to determine the positive control sample's betaine concentration, wherein the positive control sample contains betaine in a concentration representative of a cat that would benefit from the treatment; and
   comparing the feline subject's betaine concentration with the positive control sample betaine concentration, wherein the feline subject's betaine concentration being equal to or less than the positive control sample betaine concentration indicates that the feline subject would benefit from the treatment.

22. The method of claim 13, further comprising analyzing a biological sample obtained from the feline subject to determine the feline subject's 2-oxoarginine concentration; and
   comparing the feline subject's 2-oxoarginine concentration with a positive reference betaine concentration value that is representative of 2-oxoarginine concentration of a cat that would benefit from the treatment, wherein the feline subject's 2-oxoarginine concentration being equal to or greater than the positive reference 2-oxoarginine concentration value indicates that the feline subject would benefit from a treatment.

23. The method of claim 13, further comprising
   analyzing a biological sample obtained from the feline subject to determine the feline subject's 2-oxoarginine concentration; and
   comparing the feline subject's 2-oxoarginine concentration with a positive reference 2-oxoarginine concentration value that is representative of 2-oxoarginine concentration of a cat that would benefit from the treatment, wherein the feline subject's 2-oxoarginine concentration being equal to or greater than the reference 2-oxoarginine concentration value indicates that the feline subject would benefit from the treatment.

24. A method of reducing risk of calcium oxalate stone formation in a feline subject comprising the steps of:
   a) identifying the feline subject as being a feline subject that would benefit from a treatment that reduces risk of calcium oxalate stone formation according to the method of claim 1; and
   b) administering to the feline subject the composition that comprises effective amounts of one or more of betaine, green tea, fenugreek and tulsi, wherein the composition comprises 0.1 to 1.0% betaine, 0.05 to 0.50% green tea, 0.005% to 0.1% fenugreek, and 0.0001 to 0.005% tulsi.

25. The method of claim 24, wherein the feline subject is fed a nutritional composition that comprises betaine, green tea, fenugreek and tulsi.

26. The method of claim 24, wherein the feline subject is fed a nutritional composition that comprises 0.25-1.0% betaine and/or 0.20-0.30% green tea and/or 0.01% to 0.05% fenugreek and/or 0.0005-0.003% tulsi.

27. The method of claim 24, wherein the feline subject is fed a nutritional composition that comprises 0.50-0.75% betaine and/or 0.10-0.50% green tea and/or 0.02% to 0.03% fenugreek and/or 0.0010% to 0.002% of tulsi.

28. The method of claim 24, wherein the feline subject is fed a nutritional composition that comprises 0.50% betaine and/or about 0.25% green tea and/or about 0.025% fenugreek and/or about 0.0015% tulsi.

29. The method of claim 24, wherein the feline subject is fed a nutritional composition that comprises about 0.50% betaine, about 0.25% green tea, about 0.025% fenugreek and about 0.0015% tulsi.

30. A method of identifying a feline subject that would benefit from a treatment that reduces risk of calcium oxalate stone formation, wherein the treatment that reduces risk of calcium oxalate stone formation comprises administering to the feline subject a composition that comprises an effective amount of betaine, green tea, fenugreek and tulsi, wherein the composition comprises 0.1 to 1.0% betaine, 0.05 to 0.50% green tea, 0.005% to 0.1% fenugreek, and 0.0001 to 0.005% tulsi; the method comprises:
   analyzing a biological sample obtained from the feline subject to determine the feline subject's betaine concentration and/or 2-oxoarginine concentration; and
   comparing the feline subject's betaine concentration and/or 2-oxoarginine concentration with a positive reference standard for betaine concentration and/or 2-oxoarginine concentration that is representative of betaine concentration and/or 2-oxoarginine concentration of a cat that would benefit from the treatment and/or results from analyzing a positive control sample containing betaine and/or 2-oxoarginine in concentration that is representative of betaine concentration and/or 2-oxoarginine concentration of a cat that would benefit from the treatment,
   wherein the feline subject's betaine concentration being equal to or less than the positive reference betaine concentration value and/or betaine concentration in the positive control sample containing beta-amino isobutyrate and/or the feline subject's 2-oxoarginine concentration being equal to or greater than the positive reference 2-oxoarginine concentration value and/or 2-oxoarginine concentration in the positive control sample containing 2-oxoarginine concentration indicates that the feline subject would benefit from a treatment.

31. The method of claim 30 comprising:
   analyzing a biological sample obtained from the feline subject to determine the feline subject's betaine concentration and/or 2-oxoarginine concentration; and
   comparing the feline subject's betaine concentration with a positive reference betaine concentration value that is representative of betaine concentration of a cat that would benefit from the treatment, wherein the feline subject's betaine concentration being equal to or less than the positive reference betaine concentration value indicates that the feline subject would benefit from a treatment.

32. The method of claim 30 comprising:
   analyzing a biological sample obtained from the feline subject to determine the feline subject's betaine concentration;
   analyzing a positive control sample to determine the positive control sample's betaine concentration, wherein the positive control sample contains betaine in a concentration representative of a cat that would benefit from the treatment; and
   comparing the feline subject's betaine concentration with the positive control sample betaine concentration, wherein the feline subject's betaine concentration being equal to or less than the positive control sample betaine concentration indicates that the feline subject would benefit from the treatment.

33. The method of claim 30 comprising:
   analyzing a biological sample obtained from the feline subject to determine the feline subject's 2-oxoarginine concentration; and
   comparing the feline subject's 2-oxoarginine concentration with a positive reference betaine concentration value that is representative of 2-oxoarginine concentration of a cat that would benefit from the treatment, wherein the feline subject's 2-oxoarginine concentration being equal to or greater than the positive reference 2-oxoarginine concentration value indicates that the feline subject would benefit from a treatment.

34. The method of claim 30 comprising:
   analyzing a biological sample obtained from the feline subject to determine the feline subject's 2-oxoarginine concentration; and
   comparing the feline subject's 2-oxoarginine concentration with a positive reference 2-oxoarginine concentration value that is representative of 2-oxoarginine concentration of a cat that would benefit from the treatment, wherein the feline subject's 2-oxoarginine concentration being equal to or greater than the reference 2-oxoarginine concentration value indicates that the feline subject would benefit from the treatment.

35. A method of reducing risk of calcium oxalate stone formation in a feline subject comprising the steps of:
   a) identifying the feline subject as being a feline subject that would benefit from a treatment that reduces risk of calcium oxalate stone formation according to the method of claim 20; and
   b) administering to the feline subject a composition that comprises effective amounts of betaine, green tea, fenugreek and tulsi
   wherein the composition comprises 0.1 to 1.0% betaine, 0.05 to 0.50% green tea, 0.005% to 0.1% fenugreek, and 0.0001 to 0.005% tulsi.

36. The method of claim 35, wherein the feline subject is fed a nutritional composition that comprises betaine, green tea, fenugreek and tulsi.

37. The method of claim 35, wherein the feline subject is fed a nutritional composition that comprises 0.25-1.0% betaine and/or 0.20-0.30% green tea and/or 0.01% to 0.05% fenugreek and/or 0.0005-0.003% tulsi.

38. The method of claim 35, wherein the feline subject is fed a nutritional composition that comprises 0.50-0.75% betaine and/or 0.10-0.50% green tea and/or 0.02% to 0.03% fenugreek and/or 0.0010% to 0.002% of tulsi.

39. The method of claim 35, wherein the feline subject is fed a nutritional composition that comprises 0.50% betaine and/or about 0.25% green tea and/or about 0.025% fenugreek and/or about 0.0015% tulsi.

40. The method of claim 35, wherein the feline subject is fed a nutritional composition that comprises about 0.50% betaine, about 0.25% green tea, about 0.025% fenugreek and about 0.0015% tulsi.

* * * * *

UNITED STATES PATENT AND TRADEMARK OFFICE
CERTIFICATE OF CORRECTION

PATENT NO. : 11,155,856 B2  
APPLICATION NO. : 16/718836  
DATED : October 26, 2021  
INVENTOR(S) : Dennis Jewell et al.

Page 1 of 1

It is certified that error appears in the above-identified patent and that said Letters Patent is hereby corrected as shown below:

In the Claims

Column 41, Line 16, Claim 11, after "tulsi", insert -- , --.

Column 43, Line 13, Claim 24, delete "one or more of".

Column 44, Line 64, Claim 35, after "tulsi", insert -- , --.

Signed and Sealed this  
Fourth Day of January, 2022

Drew Hirshfeld  
*Performing the Functions and Duties of the*  
*Under Secretary of Commerce for Intellectual Property and*  
*Director of the United States Patent and Trademark Office*

SEQUENCE LISTING

<160> NUMBER OF SEQ ID NOS: 1

<210> SEQ ID NO 1
<211> LENGTH: 201
<212> TYPE: DNA
<213> ORGANISM: Felis catus

<400> SEQUENCE: 1

```
atatgttagt atctctacat gtgggagaac cagatgtcag gttcatgtat gatacagcag      60
gaagaacaca gcacggcctt tgaagtattc ctgtttatag raataattct ttcatatgca     120
ggtacgtgtg tgtgtgtgtg tgtgtgtgtg tgtgtgtgtg tgtgtatttt ataaaggtag     180
ctactcctta ttcatagata t                                               201
```